United States Patent
Paz et al.

(12) 
(10) Patent No.: US 7,364,553 B2
(45) Date of Patent: Apr. 29, 2008

(54) BREATH AEROSOL MANAGEMENT AND COLLECTION SYSTEM

(75) Inventors: Frederick Mark Paz, Littleton, CO (US); David Howson, Denver, CO (US); Michael V Wiernicki, Trumansburg, NY (US)

(73) Assignee: Amidex, Inc., Lakewood, CO (US)

( * ) Notice: Subject to any disclaimer, the term of this patent is extended or adjusted under 35 U.S.C. 154(b) by 333 days.

(21) Appl. No.: 10/745,331

(22) Filed: Dec. 22, 2003

(65) Prior Publication Data

US 2005/0137491 A1 Jun. 23, 2005

Related U.S. Application Data

(60) Provisional application No. 60/435,804, filed on Dec. 20, 2002.

(51) Int. Cl.
*A61B 5/08* (2006.01)

(52) U.S. Cl. ....................... 600/543; 600/529

(58) Field of Classification Search ......... 600/529–543
See application file for complete search history.

(56) References Cited

U.S. PATENT DOCUMENTS

| | | | |
|---|---|---|---|
| 3,858,573 A | 1/1975 | Ryan et al. | |
| 4,117,714 A | 10/1978 | Goodson et al. | |
| 4,202,345 A | 5/1980 | Dansky et al. | |
| 4,370,986 A * | 2/1983 | Gebhart et al. | ............. 600/529 |
| 4,947,861 A | 8/1990 | Hamilton | |
| 5,026,027 A | 6/1991 | Hamilton | |
| 5,042,501 A | 8/1991 | Kenny | |
| 5,081,871 A * | 1/1992 | Glaser | ..................... 73/863.23 |
| 5,176,723 A | 1/1993 | Liu et al. | |
| 5,361,771 A | 11/1994 | Craine | |
| 5,432,094 A | 7/1995 | Delente | |
| 5,465,728 A | 11/1995 | Phillips | |
| 5,515,859 A | 5/1996 | Paz | |
| 5,676,154 A | 10/1997 | Pettersson | |
| 5,787,885 A * | 8/1998 | Lemelson | ................... 600/309 |

(Continued)

FOREIGN PATENT DOCUMENTS

DE     196 19 763 A     11/1997

(Continued)

OTHER PUBLICATIONS

Agarwal, A.R., et al., "Expression of matrix proteins in an in vitro model of airway remodeling in asthma." Allergy Asthma Proc., vol. 24; 2003; pp. 35-42.

(Continued)

*Primary Examiner*—Robert L. Nasser. Jr.
*Assistant Examiner*—Karen E Toth
(74) *Attorney, Agent, or Firm*—Faegre & Benson LLP

(57) ABSTRACT

Aerosol collectors 10, 120 include pre-collection filters 100, 126, aerosol collection chambers 30, 130, and other exhaled breath conditioning and control features for providing not only accurate and efficient, but also reliable and reproducible aerosol collections that can be used in standardizations and can be compared in meaningful ways to other exhaled breath aerosol collections from the same test subject and from different test subjects. The aerosol collector 10 example includes electrostatic collection components 34, 40, and the aerosol collector 120 includes nucleating condensation components 168, 172 and vortex collection components 132, 138. Both include analyte extraction apparatus 50, 124.

32 Claims, 10 Drawing Sheets

U.S. PATENT DOCUMENTS

| | | | |
|---|---|---|---|
| 5,795,787 A | 8/1998 | Silkoff et al. | |
| 5,855,652 A | 1/1999 | Talley | |
| 5,996,586 A | 12/1999 | Phillips | |
| 6,010,459 A | 1/2000 | Silkoff et al. | |
| 6,033,368 A | 3/2000 | Gaston et al. | |
| 6,038,913 A * | 3/2000 | Gustafsson et al. | 73/23.3 |
| 6,051,189 A | 4/2000 | Wick et al. | |
| 6,067,983 A | 5/2000 | Stenzler | |
| 6,158,676 A * | 12/2000 | Hughes | 239/405 |
| 6,312,390 B1 | 11/2001 | Phillips | |
| 6,419,634 B1 | 7/2002 | Gaston et al. | |
| 6,443,147 B1 * | 9/2002 | Matter | 128/200.26 |
| 6,468,330 B1 | 10/2002 | Irving et al. | |
| 6,488,635 B1 * | 12/2002 | Mottram | 600/551 |
| 6,520,034 B1 | 2/2003 | Masquelier et al. | |
| 6,540,691 B1 | 4/2003 | Phillips | |
| 6,585,661 B1 * | 7/2003 | Hunt et al. | 600/532 |
| 6,623,544 B1 * | 9/2003 | Kaura | 95/3 |
| 6,656,127 B1 | 12/2003 | Ben-Oren et al. | |
| 6,726,637 B2 * | 4/2004 | Phillips | 600/543 |
| 7,004,909 B1 * | 2/2006 | Patel et al. | 600/532 |
| 2003/0023389 A1 * | 1/2003 | Rothe et al. | 702/23 |
| 2003/0109794 A1 | 6/2003 | Phillips | |
| 2003/0132380 A1 * | 7/2003 | Miller et al. | 250/286 |
| 2003/0208132 A1 * | 11/2003 | Baddour | 600/532 |
| 2003/0216660 A1 | 11/2003 | Ben-Oren et al. | |
| 2004/0161804 A1 * | 8/2004 | McCash et al. | 435/7.2 |
| 2004/0216743 A1 * | 11/2004 | Orr et al. | 128/205.12 |
| 2004/0216745 A1 * | 11/2004 | Yuen et al. | 128/205.27 |
| 2006/0054017 A1 * | 3/2006 | Haglund et al. | 95/32 |

FOREIGN PATENT DOCUMENTS

| | | |
|---|---|---|
| EP | 0 061 074 A | 9/1982 |
| EP | 650051 A2 | 4/1995 |
| EP | 759169 B1 | 1/1998 |
| EP | 573060 B1 | 2/2000 |
| EP | 1 209 223 A | 5/2002 |
| WO | WO 95/31721 A1 | 11/1995 |
| WO | WO 97/35519 | 10/1997 |
| WO | WO 97/38307 | 10/1997 |
| WO | WO 98/48045 A2 | 10/1998 |
| WO | WO 00/35337 A2 | 6/2000 |
| WO | WO 00/78447 A1 | 11/2000 |
| WO | WO 01/84112 A1 | 11/2001 |
| WO | WO 01/95991 A1 | 12/2001 |
| WO | WO 02/082977 A2 | 10/2002 |
| WO | WO 03/064994 A2 | 8/2003 |

OTHER PUBLICATIONS

Andreoli, R., et al., "Determination of patterns of biologically relevant aldehydes in exhaled breath condensate of healthy subjects by liquid chromatography/atmospheric chemical ionization tandem mass spectrometry," Rapid Commun. Mass Spectrom, vol. 17; 2003; pp. 637-645.

Antczak, A., et al., "Markers of pulmonary diseases in exhaled breath condensate." Int. J. Occup. Med. Environ. Health, vol. 15; 2002; pp. 317-323.

Becher, G., et al.; Breath condensate as a method of noninvasive assessment of inflammation mediators from the lower airways. Pneumologie, vol. 51; 1997; Suppl. 2; pp. 456-459.

Carpagnano, G.E., et al., "Increased vitronectin and endothelin-1 in the breath condensate of patients with fibrosing lung disease." Respiration, vol. 70; 2003; pp. 154-160.

Cheah, F. C., et al., "Problems associated with collecting breath condensate for the measurement of exhaled hydrogen peroxide from neonates on respiratory support." Biol Neonate., vol. 84; 2003; pp. 338-341.

Christopher, K. L., et al., "The potential role of respiratory therapy equipment in cross infection. A study using a canine model for pneumonia." Am. Rev. Respir. Dis., vol. 128; 1983; pp. 271-275.

Effros, R.M., et al., "A simple method for estimating respiratory solute dilution in exhaled breath condensates." Am. J. Respir. Crit. Care Med., vol. 168; 2003; pp. 1500-1505.

Fairchild, C.I., et al., "Particle concentration in exhaled breath." Am. J. Respir. Crit. Care Med., vol. 48; 1987; pp. 948-949.

Friedlander, S.K., "Smoke, duest and haze. Fundamentals of aerosol dynamics." Oxford, UK; Oxford University Press, 2000.

Gessner, C., et al., "Factors influencing breath condensate volume." Pneumologie, vol. 55; 2001; pp. 414-419.

Gessner, C., et al., "Exhaled breath condensate nitrite and its relation to tidal volume in acute lung injury." Chest, vol. 124; 2003; pp. 1046-1052.

Griese, M., et al., "A noninvasive method to collect nasally exhaled air condensate in humans of all ages." Eur. J. Clin. Invest., vol. 31; 2001; pp. 915-920.

Griese, M., et al., "Protein pattern of exhaled breath condensate and saliva." Proteomics, vol. 2; 2002; pp. 690-696.

Huszar, E., et al., "Adenosine in exhaled breath condensate in healthy volunteers and in patients with asthma." Eur. Respir. J., vol. 20; 2002; pp. 1393-1398.

Hychka, S.H., "[Diagnostics and prediction of development of pulmonary complications in acute myocardial infraction (morphological validation of the use of non-invasive investigational methods)]. (Ukrainian)." Lik Sprava, vol. 7; 2002; pp. 21-25.

Kharitonov, S.A., et al.; "Biomarkers of some pulmonary diseases in exhaled breath." Biomarkers, vol. 7; 2002; pp. 1-32.

Kharitonov, S.A., et al.; "Exhaled markers of inflammatory lung diseases: ready for routine monitoring?" Swiss Med Wkly, vol. 134; 2004; 175-192.

Larstad, M., et al.: "Determination of malondialdehyde in breath condensate by high-performance liquid chromatography with fluorescence detection." J. Chromatogr. B: Analyt. Technol. Biomed. Life Sci., vol. 766; 2002; pp. 107-114.

Laztin, P., et al.; "Comparison of exhaled breath condensate from nasal and oral collection." Eur. J. Med. Res. vol. 8; 2003; pp. 505-510, Montuschi, P., et al.; "Analysis of exhaled breath condensate for monitoring airway inflammation." Trends Pharmacol. Sci., vol. 23; 2002; pp. 232-237.

Montuschi, P., et al., "Validation of leukotriene B4 measurements in exhaled breath condensate." Inflamm. Res., vol. 52; 2003; pp. 69-73.

Nayeri, F., et al.; "Exhaled breath condensate and serum levels of hepatocyte growth factor in pneumonia." Respir. Med., vol. 96; 2002; pp. 115-119.

Nowak, D., et al.; "Exhalatin of H202 and thobarbituric acid reactive substances (TBArs) by healthy subjects." Free Radic. Biol. Med., vol. 30; 2001; pp. 178-186.

Scheideler, L., et al.; "Detection of nonvolatile macromolecules in breath. A possible diagnostic tool?" Am Rev Respir Dis., vol. 148; 1003; pp. 778-784.

Schreiber, J., et al.; "*Mycobacterium tuberculosis* gene-amplification in breath condensate of patients with lung tuberculosis." Eur. Respir J., vol. 7; 2002; pp. 290-291.

Van Beurden, W.J., et al.; "An efficient and reproducible method for measuring hydrogen peroxide in exhaled breath condensate." Respi. Med., vol. 96; 2002; pp. 197-203.

Vogelberg, C., et al.; "*Pseudomonas aeruginosa* and *Burholderia cepacia* cannot be detected by PCR in the breath condensate of patients with cystic fibrosis." Pediatr. Pulmonol., vol. 36; 2003; pp. 348-352.

Carpagnano, G.E., "Interleukin-6, obstructive sleep apnea, and obesity." Chest, vol. 124; 2003; pp. 1621-1622. author reply p. 1622.

Carpagnano, G.E., "Increased inflammatory markers in the exhaled breath condensate of cigarette smokers." Eur. Repir J., vol. 21; 2003; pp. 589-593.

Carpagnano, G.E., "8-Isoprostane, a marker of oxidative stress, is increased in exhaled breath condensate of patients with obstructive sleep apnea after night and is reduced by continuous positive airway pressure therapy." Chest, vol. 124; 2003; pp. 1386-1392.

Carpagnano, G.E., "Increased 8-isoprostane and interleukin-6 breath condensate of obstructive sleep apnea patients." Chest, vol. 122; 2002; pp. 1162-1167.

Carpagnano, G.E., "Increased leukotriene B4 and Interleukin-6 in exhaled breath condensatee in cystic fibrosis." Am. J. Respir. Crit. Care Med., vol. 167; 2003; pp. 1109-1112.

Corradi, M., et al., "Aldehydes in exhaled breath condensate of patients with chronic obstructive pulmonary disease." Am. J. Respir. Crit. Care Med., vol. 167; 2003; pp. 1380-1386.

Corradi, M., et al., "Aldehydes and glutathione in exhaled breath condensate of children with asthma exacerbation." Am. J. Respir. Crit. Care Med., vol. 167; 2003; pp. 395-399.

Demers, R.R., "Bacterial/Viral Filtation. Let the breather beware!" Chest, vol. 120; 2001; pp. 1377-1389.

Effros, R.M., et al., "Dilution of respiratory solutes in exhaled condensates." Am. J. Respir. Crit. Care Med., vol. 165, 2002; pp. 663-669.

Effros, R. M., "Saving the breath condensate approach." Am. J. Respir. Crit. Care Med., vol. 168; 2003; pp. 1129-1132; author reply 1130-1131.

Gaston, B., "Breath condensate analysis perhaps worth studying, after all." Am. J. Respir. Crit. Care Med., vol. 167; 2003; pp. 292-293.

Gessner, C., et al., "Exhaled breath condensate nitrite and its relation to tidal volume in acute lung injury." Chest, vol. 124; 2003; pp. 1046-1052.

Horvath, I., "Exhaled breath condensate contains more than only volatiles." Eur. Respir. J., vol. 22; 2003; pp. 187-188 [author reply].

Hyde, R.W.; "I Don't Know Why You Guys Are Measuring, But Your Sure Are Measuring It! A Fair Criticism of Measurements of Exhaled Condensates?" Am. J. Respir. Crit. Care Med., vol. 165; 2002; pp. 561-564.

Jaeger, GmbH: "Info—Special Edition, Breath Condensate." Company-assembled compendium of research using a commercial surface condenser. 1st Edition; Apr. 2001.

Kharitonov, S.A., et al.; "Exhaled markers of inflammation." Curr. Opin. Allergy Clin. Immunol., vol. 1; 2001; pp. 217-224.

Moloney, E.D., et al., "Exhaled breath condensate detects markers of pulmonary inflammation after cardio-thoracic surgery." Am. J. Respir. Crit. Care Med.; 2003; Oct. 9 [Epub ahead of print: doi10.1164/rccm.200307-1005OC].

Mutlu, G.M., et al.; Collection and Analysis of Exhaled Breath Condensate in Humans. Am. J. Respir. Crit. Care Med., vol. 164; 2001; pp. 731-737.

Mutti, A., et al.; "Reporting data on exhaled breath condensate." Am. J. Respir. Crit. Care Med., vol. 168; 2003; pp. 719 [author reply].

Risby, T.H.; "Futher discussion on breath condensate analysis." Am J Respir Crit care Med., vol. 167; 2003; pp. 1301-1302.

Spicuzza, L. et al.; "Adenosine levels in the exhaled breath condensate: a potential surrogate marker of airway inflammation." Eur. Respir J., vol. 22; 2003; pp. 392-395.

Wood, L.G., et al.; "Biomarkers of lipid peroxidation, airway inflammation and asthma." Eur. Respir. J., vol. 21; 2003; pp. 177-186.

* cited by examiner

BREATH AEROSOL MANAGEMENT AND COLLECTION SYSTEM

CROSS-REFERENCE TO RELATED INVENTIONS

This is a non-provisional patent application of the provisional patent application No. 60/435,804 entitled "Breath Aerosol Management Method and System", filed on Dec. 20, 2002, which is incorporated herein by reference for all purposes.

BACKGROUND OF THE INVENTION

1. Field of the Invention

This invention is related generally to aerosol traps, and, more particularly, to methods and apparatus for collecting aerosols in exhaled breath in a reliable and reproducible manner for diagnostic and other purposes.

2. State of the Prior Art

Exhaled breath comprises gaseous materials, such as carbon dioxide, oxygen, water vapor, and others, and non-gaseous materials, such as liquid droplets, insoluble substances, and mixtures of the two. Materials in the exhaled breath that are not in the gaseous state at the opening of the mouth or nose when exhaled are considered to be aerosols for the purposes of this discussion. Some examples of such aerosols may include airborne solid particulates, such as dust and smoke, as well as liquid droplets that comprise drugs, biological materials, and other chemicals that can be subjected to analysis, i.e., analytes.

Most standard clinical analytes, i.e., substances that are the subjects of analyses, are not volatile, thus do not evaporate, at normal physiological (body) temperatures. Nevertheless, research investigators have observed such non-volatile components as drugs, proteins, electrolytes, and other analytes in condensates from exhaled breath. In 1987, Fairchild et al., "Particle Concentration in Exhaled Breath," Am. Ind. Hyg. Assoc. J., Vol. 48, 1987, pp. 948-949, demonstrated that exhaled breath contains very finely divided and very sparse aerosols of suspended materials, with the smallest particles being smaller than 100 nanometers. Some research investigators presume, therefore, that non-gaseous materials recoverable from exhaled breath are transported in the breath by means of such aerosols in the breath.

There are numerous reports of studies in which such non-gaseous constituents (analytes) of exhaled breath have been collected along with water condensate from the breath in cold-surface condensers. In cold-surface condenser processes, exhaled breath from deep in the lungs is saturated with water vapor. Air within the upper airway of the body is slightly less humid, but it does gain some humidity over ambient air from the surrounding tissues in the airway between the lungs and lips. Thus, exhaled breath, which is a mixture of such saturated air from deep in the lungs along with such slightly less humid air in the upper airway, is quite humid. When such humid, exhaled air is directed against a cold surface, for example, a cold surface in a cold-surface condenser, the water vapor in the exhaled air condenses to liquid water, and it has been noted that the condensed water dissolves some of the non-volatile, aerosol constituents (analytes) from exhaled air that happen to come into contact with the condensed water. Unfortunately, however, such inclusion of non-volatile constituents in solution with the condensate occurs only if the non-volatile constituents happen to contact the condensation and is too inconsistent to be used for reliable, reproducible, and comparable non-volatile analyte collections.

Some non-gaseous substances in the exhaled breath are capable of indicating one or more physiological conditions of a person or animal, thus may be analytes with potential for diagnostic and other research and clinical purposes. For example, exhaled air contains some blood-borne substances and may be rich in markers that are useful in diagnosis of lung or airway diseases. One particularly interesting marker in exhaled breath, adenosine, may have the potential of indicating whether a person suffers from oxygen shortage to heart muscle (cardiac ischemia), which, if unresolved, may lead to the death of heart muscle cells, i.e., heart attack.

Unfortunately, however, measurements of aerosol analytes in exhaled breath captured by condensation and other methods prior to this invention have shown excessively high variance from one measurement to the next and have been very inconsistent. Therefore, they have not been reliable or useful for detecting or discriminating one pathological or physiological state from another. Some causes of such extreme variances in, for example, surface and other condenser methods may include: (i) Collector efficiency variations from one collection apparatus to another and even from one collection event to another with the same apparatus; (ii) The volume and flow rate of exhaled breaths may be highly variable from one person to another and even from the same person from one breath to another, thus presenting the collector apparatus with an irreproducible flow of breath material from which to collect samples; (iii) Surface condensation captures aerosol analytes only indirectly, thus previous state-of-the-art collectors may capture only non-predictable and non-verifiable portions of the aerosol analytes in the exhaled breath; (iv) Condensation may cause very high dilution of dissolved analytes, thereby leading to large and irregular losses.

SUMMARY OF THE INVENTION

Accordingly, it is an object of this invention to provide improved methods and apparatus for collecting exhaled breath aerosols.

Another object of this invention is to provide methods and apparatus for reproducible and consistent collection of specimens of exhaled breath aerosol analytes that are comparable from one test to another.

Another object of the present invention is to provide methods and apparatus for reproducible and consistent collection of specimens of exhaled breath aerosol analytes that are comparable between test values and standardized reference values for various useful analytes.

Still another object of the invention is to provide methods and systems that can be used to standardize reference values for useful breath aerosol analytes.

Other objects or uses of the invention may be perceived from the description below.

Additional objects, advantages, uses and novel features of the invention are set forth in part in the description that follows and others will become apparent to those skilled in the art upon examination of the following description and figures or may be learned by practicing the invention.

To further achieve one or more of the foregoing and other objects and uses of the invention, the apparatus may include, but are not limited to, the specific example implementations explained in the detailed description of the preferred embodiments below.

While the example collectors described herein implement the method of utilizing specific aerosol property enhancements and application of specific forces directed to those property enhancements (e.g., electrostatic charge and electrostatic force in collector 10 and mass accretion and centrifugal force in collector 120) to collect aerosols from exhaled breath, there are many other possible property enhancements that can be used and forces that can be applied, such as thermophoretic force, magnetic force, gravitational force, inertia, and aerodynamic force comprising motion imposed by a moving fluid acting against an aerodynamic drag of non-gaseous aerosols. Also, while these example collectors are designed for collecting exhaled breath aerosols, the principles of this invention are also applicable to collecting other aerosols for other purposes, for example, for bio-warfare defense, environmental air quality controls, and many others.

Another feature of this invention, which is supported by the example collectors described herein, includes the air flow conditioning and control capabilities that not only enhance the aerosol collection efficiency and effectiveness, but also make the aerosols collected quantifiable in a reliable and reproducible manner that can be compared in a meaningful way to other such exhaled breath aerosol collections from the same test subject or from other test subjects and to be standardizable for studies, possible indications of disease or absence of disease, and the like. One such parameter, aerosol collected from a certain volume of exhaled breath has been suggested as one control parameter (see Jaeger, GmbH, "Info---Special Edition, "Breath Condensate", Company-assembled compendium of research using commercial surface condenser, $1^{st}$ Edition, April 2001). However, while exhaled breath volume is a useful parameter, it is not sufficient for the purposes discussed above, because there are still too many inconsistencies in the collection efficiencies as well as in the aerosol content itself without further conditioning and controls.

For example, as discussed, if ambient aerosol is drawn into the test subject's airway during inhalation, which is highly probable without pre-collection filtering, such ambient aerosols will most likely also be in the exhaled breath and thereby contaminate, and skew any exhaled breath aerosol collections, regardless of exhaled breath volume control. Therefore, conditioning the exhaled breath by pre-collection filtering of the inhaled breath to remove ambient aerosols from the inhaled breath, as discussed herein, is an important feature provided by this invention.

Flow rate of the exhaled breath is also an important parameter, because it affects collection efficiencies of the collection process. Therefore, if flow rate of the exhaled breath through the collector is not controlled and kept within predetermined ranges for a particular collector apparatus and process, the collection results will be skewed or inconsistent, regardless of exhaled breath volume control. Further, simply instructing the test subject to "breathe normally" is insufficient, because normal breathing is different for different test subjects and is affected by the environment, stress, physical condition, illness, and even by the collection process itself. Therefore, machine control of the exhaled breath flow rate, such as is provided by the example collectors described herein, is another important feature provided by this invention.

It is also important to remove large-mass artifacts from the exhaled breath, such as food particles, sputum, expectorate, saliva, and the like, before collecting the exhaled breath aerosols, because such artifacts can also contaminate and skew aerosol collection results, regardless of exhaled breath volume control. The exhaled breath aerosol collection procedures described herein can also provide for conditioning the exhaled breath by removal of such artifacts before exposing the exhaled breath to the aerosol collection apparatus and processes.

Some fractions of an exhaled breath can yield different concentrations of certain aerosols than other fractions. For example, the first one-third to one-half of an exhaled breath comprises mostly air that has been inhaled into the test subject's upper airway, but never gets into the deep lungs, where gas exchange takes place. Therefore, concentrations of aerosols that originate in the deep lungs are higher in later fractions of the exhaled breath than in earlier fractions. Therefore, for some types of aerosols targeted for use as analytes, it may be desirable to select only the later fractions of the exhaled breaths for aerosol collections and to divert the earlier fractions away from the aerosol collection apparatus or processes. This feature of the invention can be implemented in a number of ways, including, but not limited to, detection and use of markers, for example, carbon dioxide concentration, which is also higher in the later fractions of the inhaled breath, to control such flow diversions or to turn aerosol collection apparatus and processes on and off. It can also be implemented by measuring volume fractions, for example, by measuring and diverting the first 30 percent, 50 percent, or whatever, away from the aerosol collection apparatus or process or turning on the aerosol collection apparatus or process for the remaining exhaled breath fraction. Another implementation may be time, by timing breaths and activating aerosol collection after a selected time interval from the start of a breath.

Velocity of exhaled breath flow can also influence aerosol collection results, for example, if higher velocity air flow dislodges and/or carries more of a certain aerosol out of the lungs than a lower velocity air flow. In such situations, monitoring exhaled breath velocity, which is not necessarily the same as flow rate (volumetric or mass flow rate), and activating the aerosol collection process only when velocity of flow is within certain desired ranges. However, flow velocity can be derived from flow-rate measurements and other parameters, as is within the capabilities of persons skilled in the art.

BRIEF DESCRIPTION OF THE DRAWINGS

The accompanying drawings, which are incorporated in and form a part of the specification, illustrate the preferred embodiments of the present invention, and together with the written description and claims, serve to explain the principles of the invention. In the drawings:

DETAILED DESCRIPTION OF THE PREFERRED EMBODIMENTS

Figure 1:
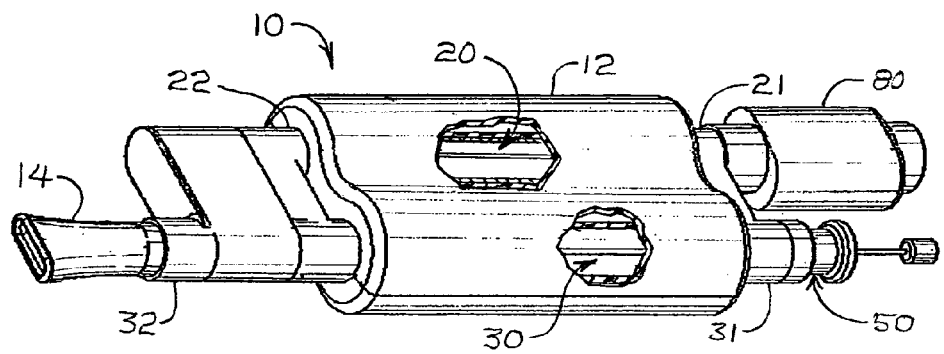
FIG. 1 is an isometric view of an electrostatic breath aerosol analyte collector according to this invention.
Figure 2:
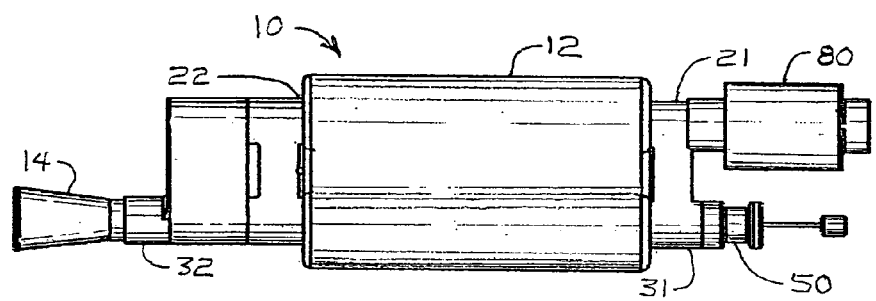
FIG. 2 is a top plan view of the electrostatic breath aerosol analyte collector of FIG. 1.
Figure 3:
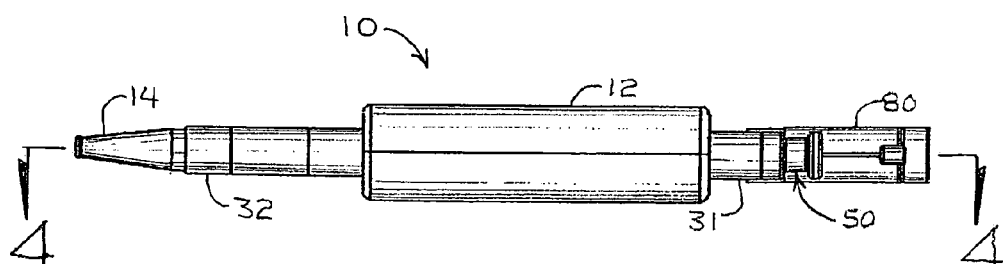
FIG. 3 is a side elevation view of the electrostatic breath aerosol analyte collector of FIG. 1.

The example breath aerosol analyte collector 10 illustrated in FIGS. 1-3 is based on electrostatic particle collection technology and provides a suitable platform for a description of some of the salient features of the invention as well as of certain details that are beneficial, albeit not essential, to the practice of the invention. Other enabling technologies and collector embodiments including, but not limited to, enhanced condensation, are described below. For this electrostatic embodiment 10 as well as other embodiments some or all of the following concepts are used to solve the problems of efficient, effective, reliable, and repeatable exhaled breath aerosol analyte collection: (1) Minimizing or eliminating contamination or skewed results from aerosols in ambient inhaled air; (2) Flow control of exhaled breath to minimize variations in aerosol analyte collection efficiencies, effectiveness, reliability, or repeatability that can result from different flow rates, pressures, time of flow, and the like; (3) Capturing substantially all aerosol materials, including smaller than 100 nanometers in mean equivalent diameter and preferably as low as 10 nanometers in mean equivalent diameter, which would include viruses; and (4) Collecting exhaled breath aerosol analytes in concentrations as high as practical for ease of detection, analysis, and other uses.

The example electrostatic breath aerosol analyte collector 10 illustrated in FIGS. 1-3 has a main housing 12 that encloses a pre-collection filter conduit or chamber 20 for removing ambient aerosol from inhaled air and a collection conduit or chamber 30 for removing exhaled aerosol analytes from exhaled breath, as will be explained in more detail below. The collection chamber is a section of the conduit 30 that surrounds the collection rod 40, so collection conduit and collection chamber are sometimes used interchangeably in relation to that section. The first end of the collection chamber is the end where exhaled breath enters the collection chamber and the second end is the opposite end. Upstream means opposite the flow direction of exhaled breath and downstream means the same direction as the flow of exhaled breath. Ambient aerosol as used herein means non-gaseous, air-borne materials in the environment around the test subject and collector, and test subject means a person or animal from which analytes are being collected. A mouthpiece 14 at one end 22 of the collection conduit 30 facilitates a test subject's inhalation of air through the pre-collection filter conduit 20 and exhalation of breath air through the collection conduit 30, although the mouthpiece 14 could be positioned at the end 22 of the pre-collection filter conduit 20 or at a variety of other locations and orientations, as will become apparent to persons skilled in the art, once they understand the principles of this invention. Suffice it to say that inhaled air is drawn through the pre-collection filter conduit or chamber 20, and exhaled breath is directed through the collection conduit or chamber 30, and the mouthpiece 14 or any number of mouthpieces can be positioned at any location or locations that facilitate those functions.

An exhaled aerosol analyte extraction assembly 50 is located at the other end 31 of the collection conduit 30 for extracting aerosol analytes that are removed from the exhaled breath in the collection conduit 30, as will be explained in more detail below. An optional flow meter 80 is also shown on the breath aerosol analyte collector 10, which can be used to control flow rate of the inhaled or exhaled breath air as well as to provide flow rate measurements used for volume control, collection of aerosol from selected fractions of exhaled breath, and other control functions, as will also be explained in more detail below.

Figure 4:
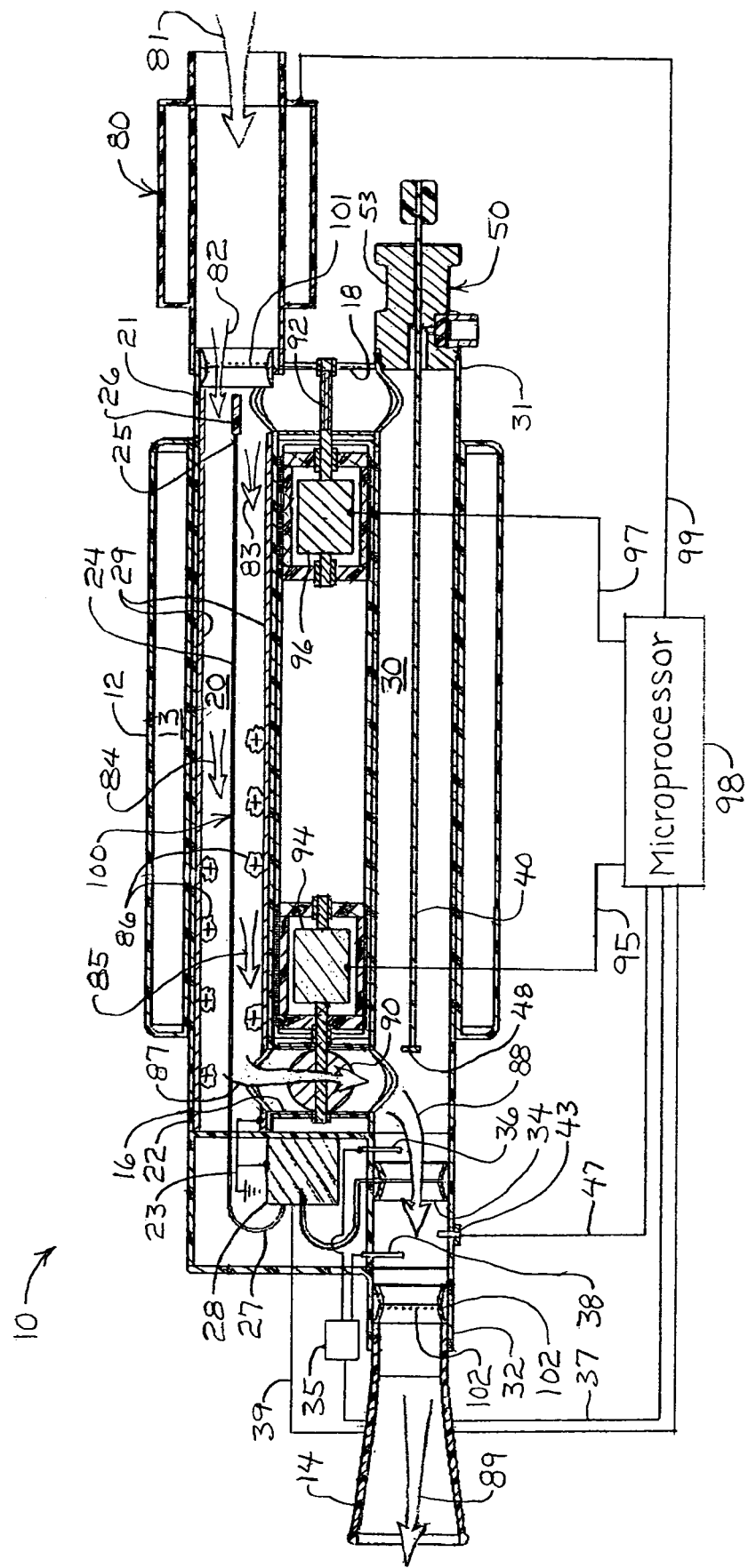
FIG. 4 is a cross-section view of the electrostatic breath analyte collector of FIGS. 1-3 taken along section plane 4-4 in FIG. 3 and illustrating an inhalation operational mode.

Referring now primarily to FIG. 4 with secondary reference to FIGS. 1-3, air during inhalation of a breath is drawn into the breath aerosol analyte collector 10 through the flow meter 80 and into the inlet end 21 of the pre-collection filter conduit 20, as indicated by the flow arrows 81, 82. The flow meter 80 is optional, but flow rate measurements from it or some other flow measuring or flow controlling device can be useful in controlling and/or characterizing or quantifying breath flow through the collector 10 for comparing results of collections of exhaled aerosol analytes from one test subject with results from other collections from the same test subject, with results from collections from other test subjects, and with standardized results or quantified indicators of presence or absence of physiological diseases, symptoms, or other problems or concerns. Some flow control can be provided by the test subject in trying to, for example, inhale and exhale in as ordinary a manner as possible during an aerosol analyte collection procedure, but control of the exhale air flow with the collection apparatus 10 itself may provide more consistency, even if the test subject is uncooperative, unconscious, or unable to comply with collection operation instructions. The flow meter 80 as described herein facilitates implementation of such control.

If a flow meter 80 is not used or if it is positioned in another location, which is an option for this invention, the air can be drawn directly into the pre-collection filter conduit 20. A pre-collection filter 100, which, in this embodiment 10, is an electrostatic filter but can be any other kind of filter that meets the pre-collection filter performance goals and/or functions described herein, is positioned in the pre-collection filter conduit 20 primarily for the purpose of removing any aerosols in ambient air flowing into the collector 10. The goal is that only exhaled breath aerosols, not aerosols from the ambient air (i.e., ambient aerosols), get collected in the collection conduit or chamber 30, which will be described in more detail below. In other words, if the air inhaled by the test subject contains ambient aerosols, at least some of those ambient aerosols are likely to also be in the exhaled breath and would probably be caught and collected in the collection conduit 30, which is preferably designed and made to collect as much of the aerosol in the exhaled breath as possible in order to collect the analytes from the exhaled breath in sufficient concentrations and quantities to be useable and meaningful. Since an object of this invention is to collect analytes in the exhaled breath that are produced in or derived from the lungs of the test subject, existence of ambient aerosols in the aerosols collected in the collection conduit would be considered contaminants. One of the objects of this invention is to minimize, if not eliminate such contamination.

It is well known, for example, that ambient air contains aerosolized solids and liquid droplets, such as dust, soot, and smoke. Less obvious, but of great concern nonetheless are living organisms and viruses, such as those associated with communicable diseases by means of airborne exposure. These kinds of ambient bio-aerosols have particular importance when dealing with collection and measurement of extremely small amounts of bio-materials contained in exhaled breath aerosol, and it is best to eliminate them from the airstream before they even get into exhaled air where they would likely be collected along with the aerosol analytes from the test subject's lungs. For example, it is typical that a first portion of exhaled air volume, when a test subject is at rest, comprises reflux of inhaled air with little modification. This first portion or fraction represents the volume of inhaled air that travels no deeper than the upper airways (mouth and nasal passages, pharynx, trachea, and upper bronchi) and never gets into the test subject's lungs. These upper airway structures do not participate in gas exchange and present a high ratio of volume to surface area relative to that seen within the lungs at the alveolar (gas exchange) level. Therefore, inhaled air that traverses no further than the upper airway remains substantially unmodified except for gain of some relative humidity from water that evaporates from the liquid film in the linings of these passageways. In addition, these large diameter structures of the upper airway provide little or no filtering of aerosols from inhaled air, especially if the test subject does not inhale through the nasal passages, which do provide some small amount of filtering, but not enough to remove all or even most ambient aerosols. Consequently, some proportion of aerosols borne in inhaled gas, such as ambient air, will remain suspended in the first one-third to one-half of the breath volume that is subsequently exhaled. These ambient aerosols in the exhaled breath are very likely to be collected along with aerosol analytes produced in or derived from the test subjects lungs (endogenous aerosol) in the collection conduit 30 of the collector 10, and, in typical situations, the total mass of such ambient aerosol contaminants far exceeds the mass of endogenous aerosol generated when the test subject exhales. Furthermore, the mass of particles attributable to actively metabolizing bacteria and biocontaminants such as viruses and spores may produce bio-molecules that directly increase or metabolically reduce the measured quantity of the endogenous aerosol analytes that are the targets of the collection process. Therefore, a pre-collection filter, such as the pre-collection filter 100 in the example collector 10, placed between the source of inhalant gas (e.g., ambient air inlet 21) and the test subject's mouth or nose can minimize, if not eliminate such ambient aerosol contaminants.

While many variations and structures of electrostatic and other kinds of filter apparatus are available and can be adapted for use in this invention, the example electrostatic filter 100 in this embodiment 10 comprises a small diameter electric wire 24 (sometimes called a "corona wire"), which extends longitudinally through the pre-collection filter conduit or chamber 20 and is surrounded by an electrically conductive side wall 29 of or on the conduit or chamber 20. The pre-collection filter conduit 20 and the components of the electrostatic filter 100 are preferably sized to introduce little, if any perceivable resistance to the test subject's inhalation efforts, which is one benefit of this single wire 24 design. The wire 24 is anchored at one end 25 to a non-conductive cross-bar 26 and the other end 27 is connected to a high voltage power supply 28. The inside wall of the pre-collection filter conduit 20 comprises an electrically conductive material 29, such as metal (for example, stainless steel), conductive plastic, or other conductive material and is connected electrically to the opposite pole of the high voltage power supply 28. As explained in more detail below, it is preferred, but not essential, that the corona wire 24 be connected to the positive (+) voltage supply terminal, so the conductive wall material 29 is connected to the negative (−) voltage supply terminal, which is often called "ground", as indicated symbolically at 23. The conductive material 29 can be a separate component, a coating on the wall, or the wall material itself. When the wire 24 is charged with a high voltage, for example, in a range of 2,000 to 12,000 volts, depending on the diameter of the corona wire 24, size of the conduit or chamber 20, and other factors, and the side wall 29 is at opposite in polarity (ground) to the wire 24, it creates corona around the wire 24 that ionizes molecules in the air, which imparts a static electric charge to aerosols in the air that flows, as indicated by flow arrows 84, 85, through the pre-collection filter conduit 20. Consequently, such charged aerosols will cling to the grounded or opposite polarity of the inside wall 29, as indicated in exaggerated scale at 86. The wire 24 is preferably positive, so that ozone production is minimized, although it could be negative, if desired. Consequently, when the air flow, indicated flow arrows 87, 88, 89, reaches the mouthpiece 14 and is inhaled by a test subject (not shown) drawing a breath through the collector 10, it is substantially free of aerosols. Therefore, aerosols collected from the exhaled breath, which will be described below, will include substantially only aerosols introduced by the test subject's lungs and by the airway between the test subject's lungs and lips (not shown). An optional grounded mesh 102 in the end 32 of the conduit 30 just before the air flow is inhaled through the mouthpiece 14 neutralizes any remaining ions and collects any remaining aerosol that did not get captured on the wall 29 of the electrostatic filter 100. It also prevents someone from poking a finger or instrument into the high voltage ionizer assembly 34, which will be described below, and thereby prevent possible damage to the apparatus as well as electric shock to the test subject or other user.

As indicated by the flow arrow 87, a first valve 90, which is illustrated as a butterfly valve in FIG. 4, in the aft cross-over conduit 16 is positioned in a manner that does not impede the flow of air to the mouthpiece 14 during the inhalation of air by the test subject. At the same time, a second valve 92, also illustrated as a butterfly valve, in the fore cross-over tube 18 is closed during inhalation to prevent the ambient air from by-passing the filter 100 in the pre-collection filter conduit 20 by flowing through the collector conduit 30 to the mouthpiece 14.

The first and second valves 90, 92 do not have to be butterfly valves. On the contrary, they could be any of myriad active or passive air control valves, including, but not limited to, one-way, self-actuating check valves, as is understood by persons skilled in the art. However, the butterfly valves 90, 92 have some advantages in that they are simple and inexpensive, yet can be activated for partial closure, full closure, or full open, thus can be used to control flow rate as well as to simply open and close the air flow. In the example of FIG. 4, each butterfly valve 90, 92 is operated by a separate, single-turn brushless actuator or motor 94, 96, such as those manufactured by Saia-Burgess of Murten, Switzerland.

The flow meter 80, as mentioned above, is optional. However, flow rate measurements during inhalation and exhalation can provide a number of benefits in addition to the use for flow rate control, as mentioned above. For example, a test subject's inhalation pattern might affect the generation of exhaled breath aerosol. Relevant characteristics of the inhalation pattern may include flow rates, depth of inhalation, time between inhalation and exhalation (e.g., "holding" one's breath), timing and counting number of breaths in a collection period, or exhalation preceding the tested inhalation, pressure variations, or other properties. Flow rates multiplied by time can provide volumes of breaths or fractions of breaths and can be provided by the microprocessor 98 on a real time basis for control of collector functions during inhalation and exhalation as well as being recorded for post-collection analysis purposes. Therefore, data about inhalation flow rates and other patterns, in addition to enabling collector control functions may also enable correction or compensation, or at least explanations for deviations in, analytical data from the collected exhaled breath aerosol analyte specimens.

The flow meter 80 can be a hot wire anemometer or any other flow meter type that measures gas flow rates accurately. If desired, the flow meter 80 can be connected to a microprocessor, illustrated schematically at 98, or any other circuit or device for recording, displaying, or outputting flow rate measurements and/or for controlling the opening, closing, and flow metering functions of the valves 90, 92, as is within the capabilities of persons skilled in the art, once they understand this invention. The actual microprocessor 98, electrical connections 95, 97, 99, and other electric circuits and components can be positioned in the annular space 13 enclosed by the housing 12 or in any other convenient locations.

Figure 5:
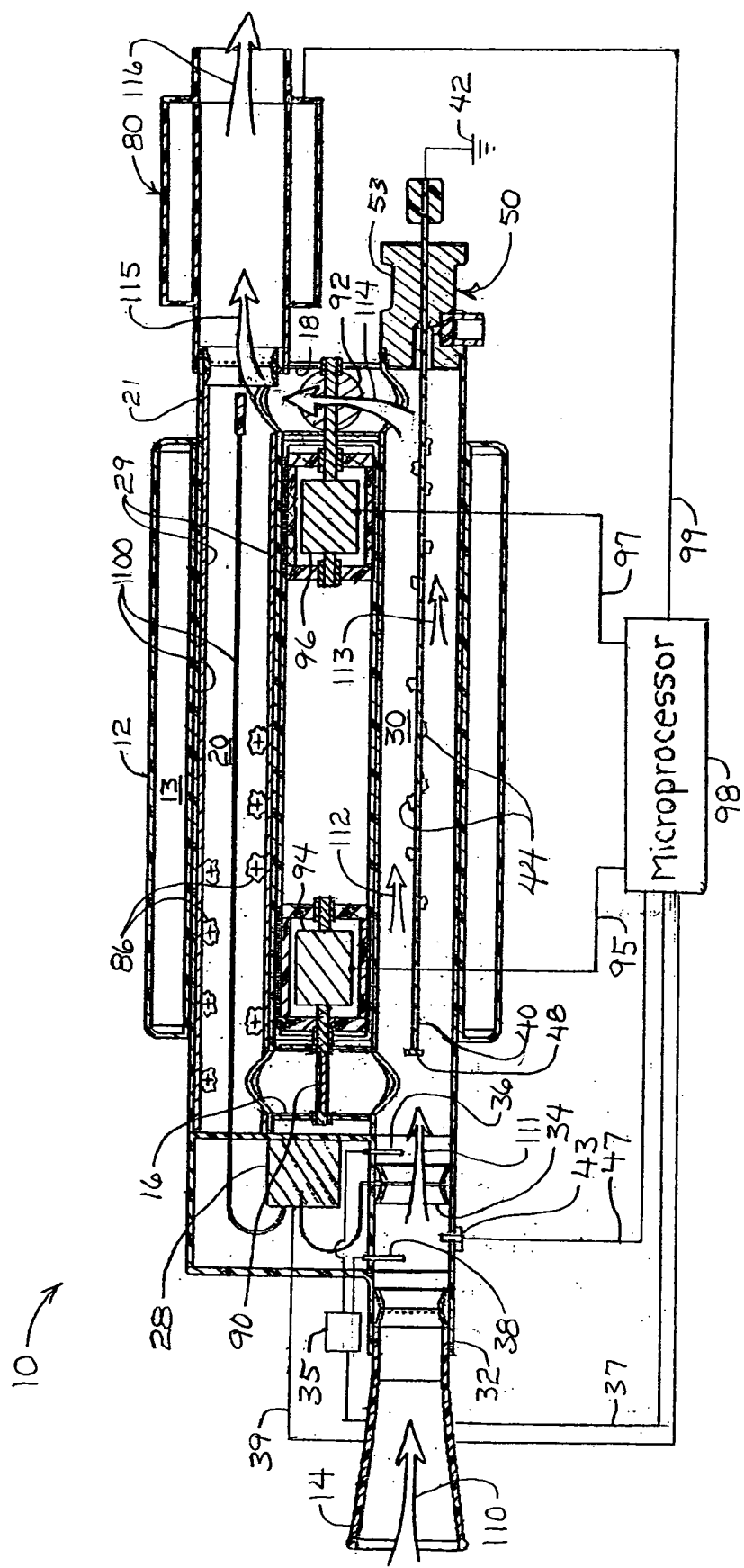
FIG. 5 is a cross-section view similar to FIG. 4, but illustrating an exhalation operation mode.

After the breath of air with the ambient aerosols removed is inhaled through the collector 10 by the test subject (person or animal), the test subject exhales the breath into the mouthpiece 14, as indicated by the flow arrow 110 in FIG. 5. In the exhale mode, the first butterfly valve 90 is closed, and the second butterfly valve 92 is opened to allow the exhaled air to flow, as indicated by flow arrows 111, 112, 113, 114, 115, 116, through the collection chamber 30, flow meter 80, and out of collector 10.

Also, in the exhale mode, an ionizer assembly 34 positioned in the collection conduit 30 upstream from a grounded (i.e., negative voltage potential) collection rod 40 is turned on to ionize exhaled air and thereby create electrostatic charges in any aerosols, including analytes in the exhaled breath. The corona wires 104 of the ionizer system 34 (FIG. 9) are preferably connected to the positive (+) terminal of the high voltage power supply 28, so, as explained above, the term "grounded" for the collection rod 40 means it is connected electrically to the negative (−) terminal of the power high voltage power supply 28, as indicated by the "ground" symbol 42. Again, since practically all of the ambient aerosol 86 was removed from the inhaled air in the pre-collection filter 100, as explained above, substantially all of the aerosols in the exhaled air are derived from the test subject's lungs and airway. As the positive charged, ionized air flow 112, 113 from the ionizer system 34 continues through the collection tube 30, the airborne, positive charged aerosols from the test subject's lungs flow past the collection rod 40, which extends from the extraction assembly 50 toward the ionizer assembly 34. As mentioned above, the collection rod 40 is at negative (−) potential (i.e., grounded, as indicated by the ground symbol 42, so the positive charged aerosol are attracted to, and cling to, the negative charged collection rod 40, as illustrated in somewhat exaggerated sizes at 44. Preferably, most, if not all, of the aerosol analytes in the exhaled breath are collected on the collection rod 40 before the exhaled air flows out of the collection chamber 30. The longer the collection conduit 30 and rod 40, and the slower the exhaled air flow through the collection conduit 30, the more complete the aerosol analyte removal from the exhaled air will be. Therefore, it may be desirable to control the velocity or flow rate (volumetric and/or mass flow rate) of exhaled air flow 112, 113 through the collection conduit 30 as well as the volume of exhaled air for accuracy and efficiency as well as for standardization, reliability, reproducibility, and other purposes. In the example collector 10, flow rate measurements by the flow meter 80 can be fed by the connection or link 99 to the microprocessor 98 for use in adjusting the valve 92 in the fore cross-over conduit 18 to maintain the exhaled air flow velocity or flow rate in the collection conduit 30 in a desired range.

There is no significant detriment to lack of moisture in electrostatic collection of aerosol particles, so there is no need for provisions in collector 10 to maintain humidity in the exhaled air before and during collection of aerosol on the collection rod 40. In fact, there are advantages to dryer airflow and dryer aerosols for electrostatic collections, so it may be desirable in some applications to add some kind of dryer, such as a heater (not shown) to the collector 10, for example, between the grounded mesh assembly 102 and the ionizer assembly 34 to dry the exhaled air and aerosols before undergoing the electrostatic aerosol collection.

Any desired number of breaths can be inhaled and exhaled by the test subject through the collector 10 as the exhaled breath aerosol analytes are collected on the collection rod 40. If the valves 90, 92 are of a type that have to be driven from closed to open positions and vice versa, as opposed to self-actuated, one-way check valves, some kind of sensor may be used to facilitate actuation of the valves 90, 92 to open and close the cross-over conduits 16, 18 as required to direct inhale air flow through the pre-collection filter conduit 20 and to direct exhaled air flow through the collection conduit 30. While myriad sensor systems would work for this purpose, the collector 10 is illustrated, for example, with a pair of ion detectors 36, 38 positioned on opposite sides of the ionizer assembly 34. The second ion detector 38 is grounded. If there are ions in the air flow that contacts the first ion detector, a current can be detected by an ammeter 35 or other suitable detector. The ionizer assembly 34 can be at least at a low level that produces enough ions in the air flow to be detected by the ion detectors 36, 38. Because most, if not virtually all of the ions in the air flow through either conduit 20 or conduit 30 get eliminated by the grounded components 29, 40, air flow past the first ion detector probe 36 during inhalation will produce little or no current at ammeter 35. This condition can be used to indicate inhalation and, for example, can be communicated to the microprocessor 98 via connection or link 37 for use in generating control signals on links 95, 97 to the valve actuators 94, 96 to open valve 90 and close valve 92 for the inhalation mode, i.e., to direct inhalation air through the pre-collection filter conduit 20 and not through the collection conduit 30. Conversely, when air is being exhaled by the test subject, air flow through the ionizer assembly 34, as indicated by flow arrow 111 in FIG. 5, causes ionized air to contact the ion detector problem 36 to produce a current at ammeter 35. This condition can be communicated to the microprocessor 98 or other suitable circuit to activate the exhale mode, i.e., to close the valve 90 and open the valve 92 to direct exhaled air flow through the collection conduit 30 and not through the pre-collection filter conduit 20. The microprocessor 98 can also communicate via a link 39 to an appropriate circuit associated with the high voltage power supply 28 to turn up the power on the ionizer assembly 34 during exhaled breath for better aerosol analyte collection during exhalation and to turn down the power on the ionizer assembly 34 during inhalation.

As mentioned above, because exhaled breath aerosols are few and difficult to collect, analyze, quantify, characterize, and standardize, it is helpful to collect them in the highest practical concentrations. As also mentioned above, the first one-third to one-half of a typical exhaled breath is reflux of inhaled air that never reaches the lungs where alveolar gas exchange occurs and aerosol analytes of interest are produced. Therefore, it is known, for example, that carbon dioxide exchanged during respiration appears at highest concentrations in the later fractions of an exhalation, and it is quite probable, albeit not yet proven, that higher concentrations of exhaled breath aerosols are also highest in the later fractions of exhaled breaths. Consequently, it may be desirable to have the capability of starting collection of exhaled breath aerosol only when the later fractions of the exhaled breaths pass through the collection conduit or chamber 30.

This kind of collection procedure can be implemented in a number of different ways. For example, it can be done by manually turning on the electrostatic collection components, e.g., the ionizer system 34, for the collection conduit or chamber 30 only after a first fraction (e.g., one-third to one-half) of the exhaled breath has been released. It can also be accomplished by turning on the same components with a timer, for example associated with the microprocessor 98, after a preset time has elapsed from detection of the start of an exhalation. A similar effect can be attained by delaying the opening of the second valve 92 and closing the first valve 90 to prevent collection of aerosol from the first fraction of the exhaled breath on the collection rod 40. Volume, calculated with flow-rate measurements and time, can also be used as an input criteria, either alone or with other input data or criteria to control the collector 10 component functions for this purpose. Another approach (not shown) may be to provide another outlet port from the collection conduit or chamber 30, such as a lateral side port, along with a valve that can be opened when the marker, e.g., carbon dioxide, level is below the desired collection concentration level or threshold to simply vent the first portion or fraction of the exhaled breath out of the system until the marker level rises to a threshold at which collection of aerosol is desired. However, a more precise and automated system for collection of exhalation from a more aerosol-rich fraction of the exhaled breath, instrumental sensing of a suitable marker in the exhaled breath, for example, but not for limitation, carbon dioxide, can be used to start and/or stop certain collection components, such as the ionizer system 34 or valve actuators 94, 96, a valve (not shown) to vent the first fraction of the exhaled breath out of the system until the marker rises to a desired level or concentration for collection, or the like. Therefore, for example, a carbon dioxide detector 43 is shown near the entrance end 32 of the collection conduit 30 for sensing concentration of the carbon dioxide in exhaled breaths for use in starting exhaled breath aerosol collection only after carbon dioxide concentrations reach some predetermined threshold level. The carbon dioxide detector 43 can be connected to the microprocessor 98, as indicated schematically by link 47, if desired so that the threshold and responsive functions can be processed and controlled, as is within the capabilities of person skilled in the art, once they understand the principles of this invention. A suitable carbon dioxide detector for this purpose may be, for example, a respiratory capnometer, such as the model V8200 manufactured by Harvard Apparatus of Hollister, Mass., or any other carbon dioxide detector operated on a suitable circuit as is within the capabilities of persons skilled in the art.

As can be seen from the example exhaled breath aerosol collector 10 described above, it implements one of the principles of improved exhaled breath aerosol collection according to this invention, i.e., identifying a property of exhaled breath aerosol that can be enhanced to become more responsive to application of a force that enables improved collection and then applying such a force to the exhaled breath aerosol. In the electrostatic collection example of collector 10, the property, a possible electrostatic charge of some of the aerosols, is enhanced to a strong and more uniform electrostatic charge of known polarity for most, if not all, of the exhaled breath aerosol particles and/or droplets, which can be accomplished by surrounding the aerosol particles and/or droplets with charged ions which impart charges to the exhaled breath aerosol and then applying electrostatic force to collect the aerosol particles and/or droplets on the collection rod 40.

When the predetermined number of breaths or other desired criteria, such as volume of breath processed by the collection chamber at a desired or regulated flow rate, have been met to terminate the exhaled breath aerosol analyte collection, the collector 10 can be removed from the mouth of the test subject to extract the collected aerosol analytes for further processing and/or analysis. Again, there are myriad ways that such extraction can be done, but the collector 10 described above has an extractor assembly 50 at one end of the collection conduit, as shown in FIGS. 1-5. The extractor assembly 50 is best seen in FIG. 6, which is an enlarged cross-section of the extractor assembly 50 similar to the cross-section in FIGS. 4 and 5.

Essentially, to extract the exhaled aerosol analytes 44, which are captured on the surface 41 of the collection rod 40, as described above, a blunt needle 61 of a syringe 60 is pushed through a septum 51 to inject just enough liquid solvent to fill an annular space 52 around the rod 40 in the body 53 of the extraction assembly 50. The liquid solvent will usually be a kind of high purity water, such as high performance liquid chromatography (HPLC) grade water, although other suitable solvents can be used, for example, but not for limitation, any of a number of buffer solutions that are widely used in bio-chemical analysis techniques and procedures. If desired, the collector 10 can be turned and held with the bore 55 in the body in a vertical orientation during this extraction phase so that gravity helps to retain the liquid solvent in the annular space 52, although capillary action may be sufficient to retain the liquid solvent in the space 52 in other orientations. Then, the collection rod 40 is pulled longitudinally through a seal 54, as indicated by arrow 45, which wipes or scrapes the analytes 44 off the surface 41 of rod 40, where they are retained and dissolved into the liquid solvent in the annular space 52.

When enough of the rod 40 has been pulled through the seal 54 to wipe or scrape substantially all of the analytes 44 off the rod surface 41, the solvent along with the dissolved analytes can be drawn by the syringe 60 out of the space 52. The analytes can then be recovered from the solution in the syringe 60 by conventional laboratory or commercial processes for whatever further analysis or study is desired. An optional limit stop, such as a flange 48 (FIG. 5), can be provided on the end of collection rod 40, if desired, to prevent accidental removal of the rod 40 from the body 53 of the extractor assembly 50.

Figure 6:
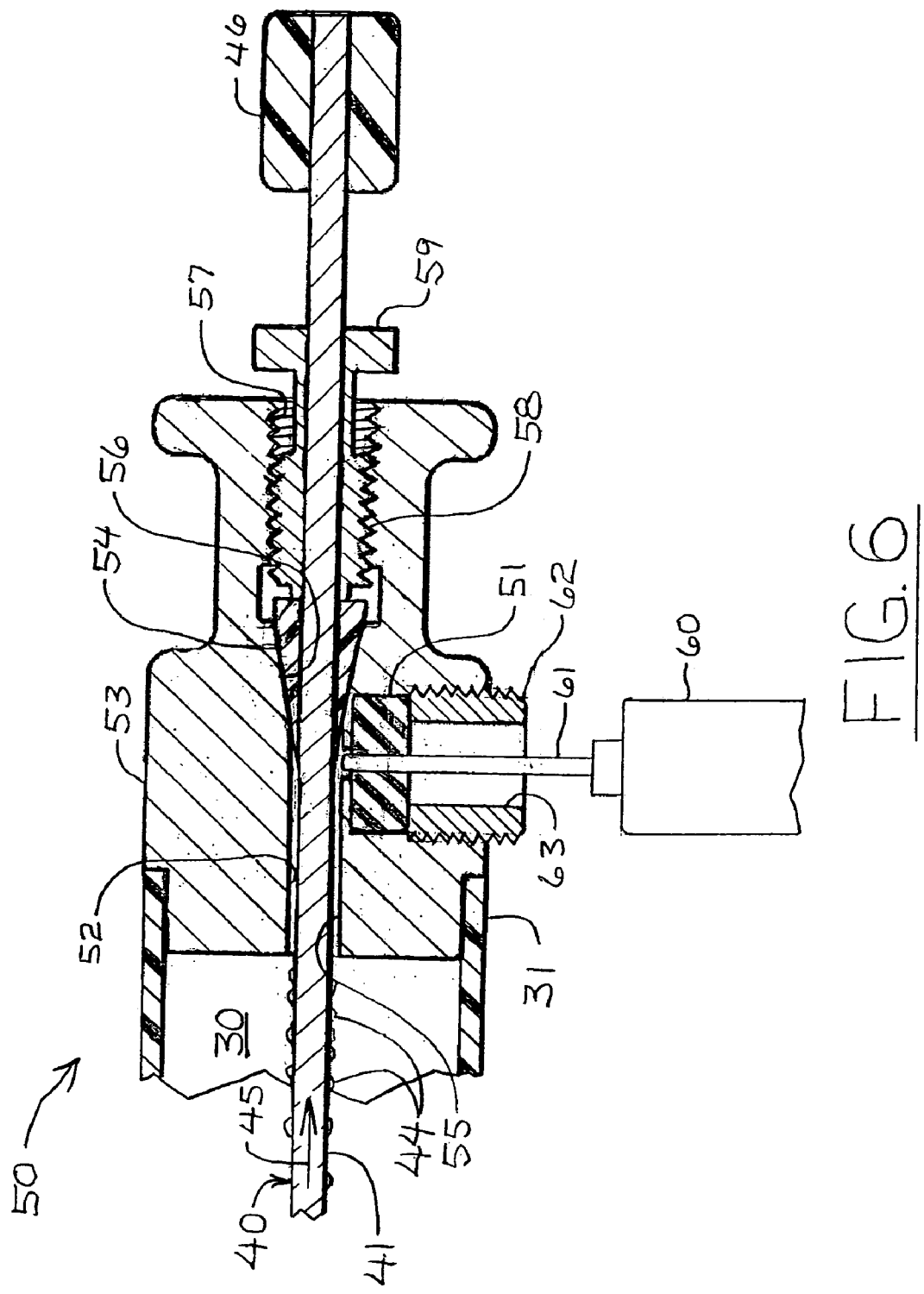
FIG. 6 is an enlarged cross-section view of the extractor assembly of FIGS. 4 and 5.

As illustrated in FIG. 6, the extraction assembly can be made with an initial axial bore 55 extending longitudinally through the body 53 with a diameter that is large enough to leave the annular space 52 between the collection rod 40 and the body 53, when the rod 40 is positioned in the bore 55. The bore 55 then widens in the mid-section of the body at 56 to accommodate the seal 54. The seal 54 and corresponding widened bore 56 can be cylindrical or any other convenient shape, but a preferred shape is tapered or conical, as illustrated in FIG. 6, to accommodate uniform snugging of the seal 54 onto the rod 40 for an effective seal against solvent leakage and for effective wiping or scraping of the analytes off the surface of the rod 40. A distal end portion 57 of the bore can be threaded to receive a threaded gland 58 for tightening and retaining the seal 54 in place. The more the gland 58 is tightened against the seal 54, the more the tapered surface of the bore section 56 squeezes the seal 54 against the rod 40. The seal 54 can be made of any of a number of suitable materials, such as PEEK™ (polyaryletherketone), which is available from Upchurch Scientific, of Oak Harbor, Wash. PEEK™ is preferred because of its strength, rigidity, chemical and physical inertness, high dielectric strength as an insulator, and compatibility with sterilization techniques. A flange 59 on the distal end of the gland 58 can be shaped to accommodate a tool, such as a wrench (not shown) for tightening, and it can serve in combination with a knob 46 on the end of the collection rod 40 as a limit stop to limit longitudinal movement of the rod 40 into the conduit 30. The collection rod 40 can be made of stainless steel or other suitable electrically conductive material, and it is preferred to have a surface roughness of no more than 200 nanometers so that the seal 54 can effectively wipe or scrape the small analyte particles 44 off the rod surfaces. Longitudinal, rather than radial scratches or roughness is also helpful in this regard, although any scratching or roughness is preferably minimized as much as practical.

The septum 51, which is preferably resilient elastomeric or flexible latex or some other resilient material that accommodates puncturing by the needle 61 and that will seal around the needle 61 to prevent leakage and reseal itself when the needle is removed, can be held in place in a transverse bore by a hollow gland 62 screwed, as shown in FIG. 6, or glued or friction held (not shown) in the body 53. The hollow bore 63 in the gland 62 accommodates insertion of the needle 61 into the septum 51. If desired, the septum 51 can be pre-split to accommodate insertion of a blunt needle 61. Also, a valve, such as those used in intervenous connections could be used in place of the septum 51.

Figure 7:
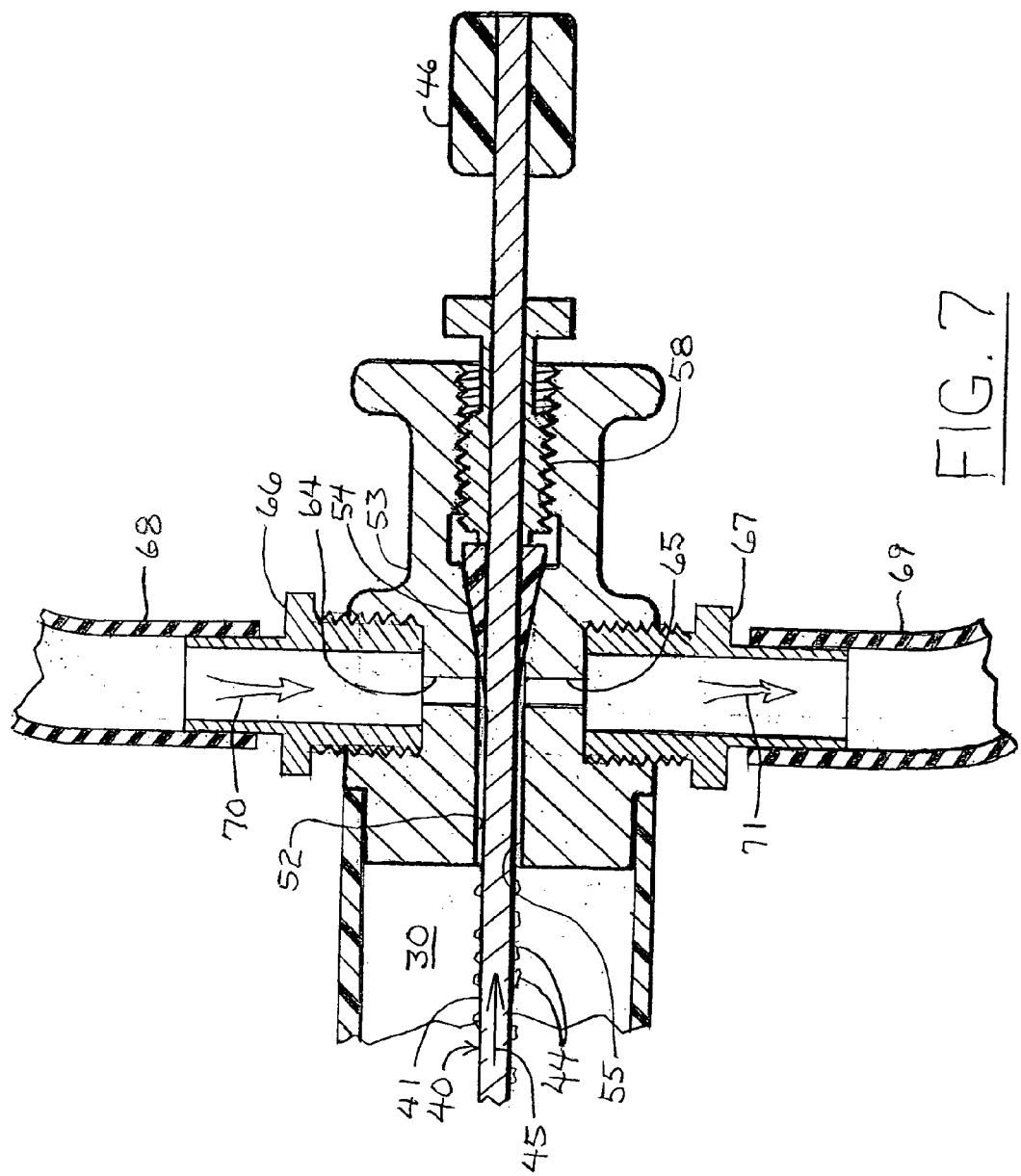
FIG. 7 is a cross-section view similar to FIG. 6, but illustrating a continuous solvent flow variation of the extractor assembly.

An alternative to the septum 51 and syringe 60 can be the arrangement shown in FIG. 7, wherein there are two conduits 64, 65 extending radially in different directions from the bore 55. A pair of fittings 66, 67 fastened to the body 53 in alignment with the conduits 64, 65 connect tubes 68, 69 to the respective conduits 64, 65, so that the liquid solvent can be flowed transversely, as indicated by arrows 70, 71 through the bore 55 adjacent the seal 54 as the collection rod 40 is drawn through the seal 54 or after the rod 40 is drawn through the seal 54. As the analytes 44 are scraped or wiped off the surface 41 of the collection rod 40, the solvent flow 70, 71 dissolves them and carries them through the downstream tube 69 to any suitable receptacle or process (not shown), where they can be recovered by conventional techniques for further analysis, classification, or study.

Figure 8:
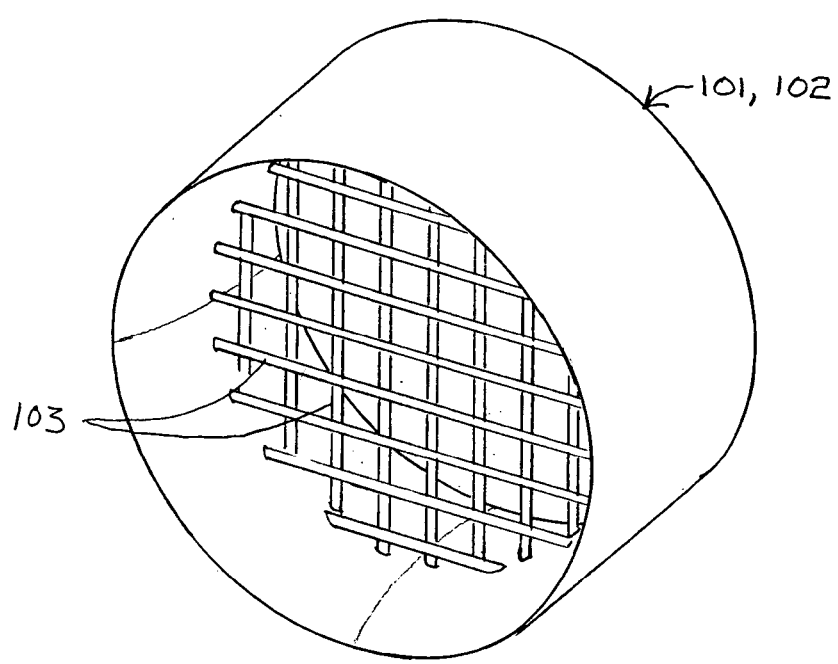
FIG. 8 is an isometric view of an example mesh assembly component.
Figure 9:
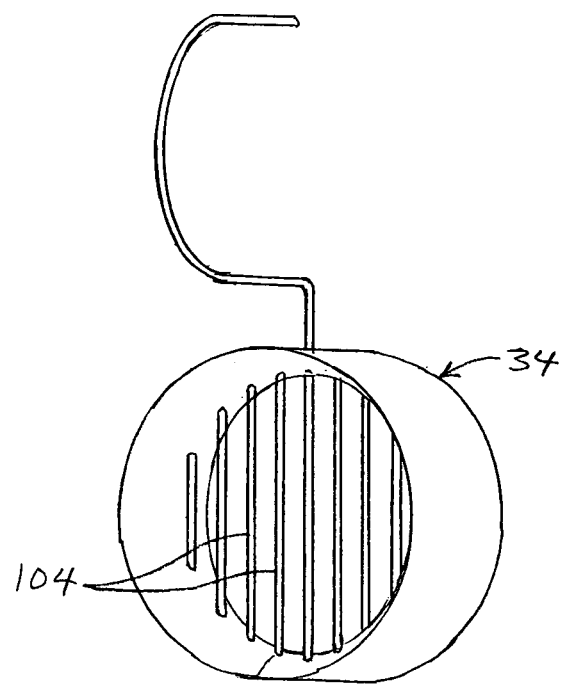
FIG. 9 is an isometric view of an example ionizer assembly.

Referring again primarily to FIGS. 4 and 5, a first grounded mesh assembly 101 is positioned at the entrance to the pre-collection filter conduit 20 and a second mesh assembly 102 is positioned at the entrance to the collection conduit 30. These grounded mesh assemblies 101, 102 prevent a person from inserting an object or finger into the high voltage ionizer elements 24, 34, respectively. They can also stop large particles, such as dust, insects, food particles, saliva, sputum, expectorate, and the like from entering the conduits 20, 30. Generally, these and other artifacts, which are larger than about 10 microns mean equivalent diameter are prevented from entering the collection chamber by the mesh assembly 102 or by any other convenient trap or device. An example grounded mesh assembly 101, 102 as shown in FIG. 8 (not to scale), and an example ionizer assembly 34 is shown in FIG. 9 (not to scale). Both are made of electrically conductive materials. The screen 103 of the mesh assembly 101, 102 can be, for example, 100 mesh fabricated with 500 micrometer tungsten or stainless steel wire, which conveniently has no more than 10% blockage of flow area through the screen 100, which may be desirable so that the test subject does not feel significant resistance by the collector 50 to exhalation effort, but is not a requirement. Of course, the flow regulation provided by the flow meter 80, microprocessor 98, valves 90, 92, and other components may present some resistance to exhalation by the test subject, especially if the test subject tries to exhale too rapidly or otherwise outside the breath flow criteria applied by these components for accuracy, reproducibility, standardization, comparability, and the like. The ionizer 34 can comprise a plurality of small diameter tungsten wires 104 (e.g., 250 micrometers) positioned parallel to each other and perpendicular to the air flow 88 (FIG. 5). They are raised to a positive potential sufficient to produce an ionized field in air, for example, 2,000 to 12,000 volts, or about 70 kV/m. The positive potential for the ionized air flow is preferred over negative to reduce ozone production, but negative may be more useful for some applications.

There are many other possible variations that can be devised to practice this invention. For example, but not for limitation, the inhaled air and exhaled air do not have to be routed through the same flow meter 80, which is optional, or even through the same entrance end 21. In fact, the pre-collection filter conduit 20 and the collection conduit 30 could be separate, each with its own respective mouthpiece, which would simply require the test subject to inhale from one of the mouthpieces through the separate pre-collection filter conduit or chamber 20 and then to exhale through the other of the mouthpieces into the collection conduit. While this maneuver would add a slight complexity for the test subject, it could eliminate the valves from the apparatus and still accommodate practicing the invention. Also, such mouthpieces 14 can have any convenient shape or structure other than that shown in FIGS. 1-5, such as a face mask with a breath port, an endotrachial tube, or any other device for capturing the air flow of a test subject's breath and channeling it through components in collector 10.

Also, as mentioned above, there are many possible valve variations that can be used to practice the invention. For example, but not for limitation, the electrostatic collection rod 40 could be replaced with any other shape or apparatus that will collect the charged aerosol analytes and from which such analytes can be recovered to practice this invention. Also, the butterfly valves 90, 92 could be mounted on a common shaft, but rotated 90 degrees in relation to each other, and actuated by one actuator or motor. In such an arrangement, rotation of the shaft in one direction would open one valve 90 as the other valve 92 is closed, and vice versa. Also, the valves could be operated manually. Such manual operation would add some complexity for the user, but the apparatus would be less complex and less expensive. On the other hand, further automation can be added to practice the invention. For example, but not for limitation, the collection rod 40 could be a continuous wire drawn automatically through the collection chamber 30 and extraction assembly 50, especially in combination with the continuous solvent flow 70, 71 of the alternate embodiment shown in FIG. 7.

Figure 10:
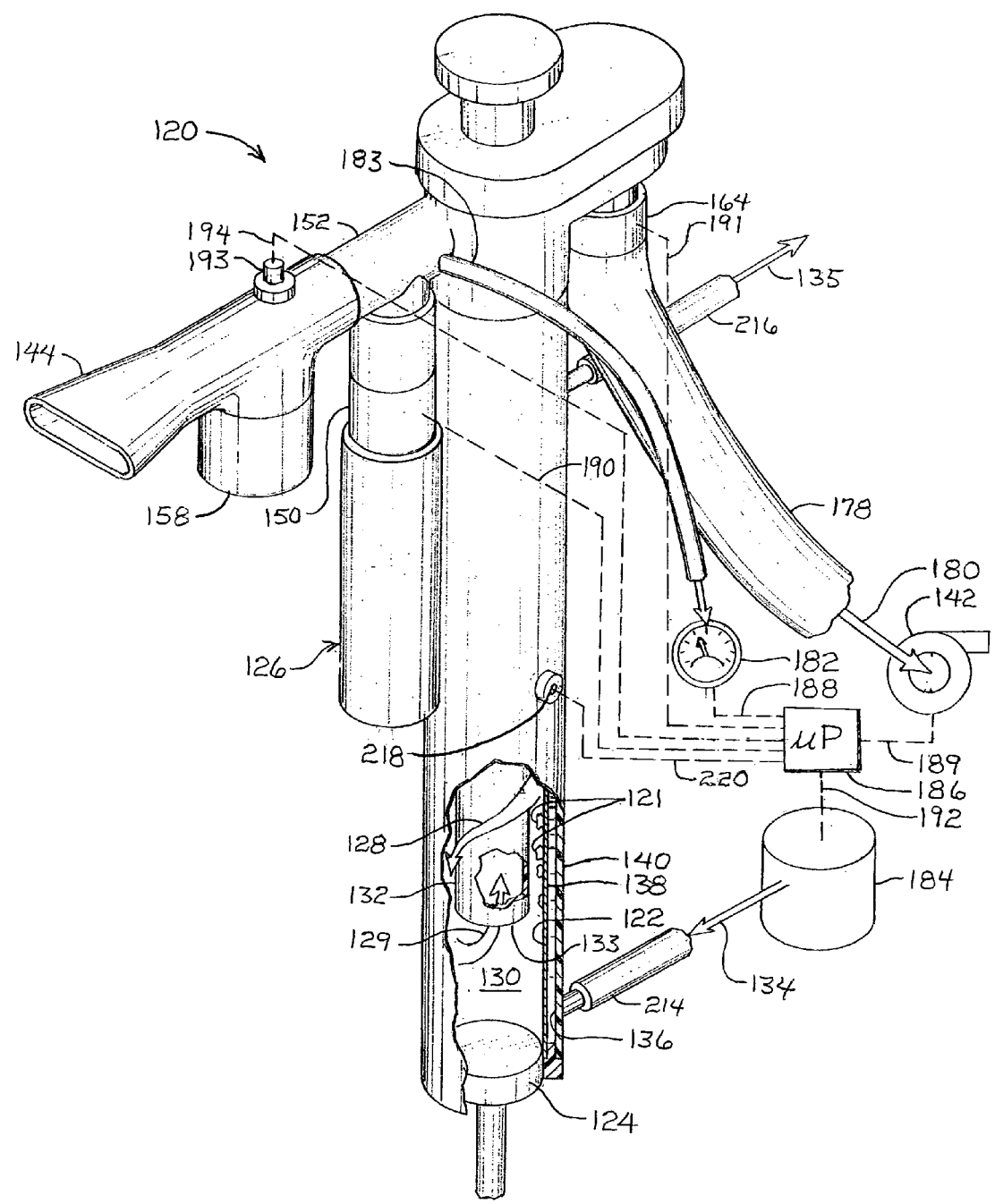
FIG. 10 is an isometric view of an enhanced condensation analyte collector according to this invention.
Figure 11:
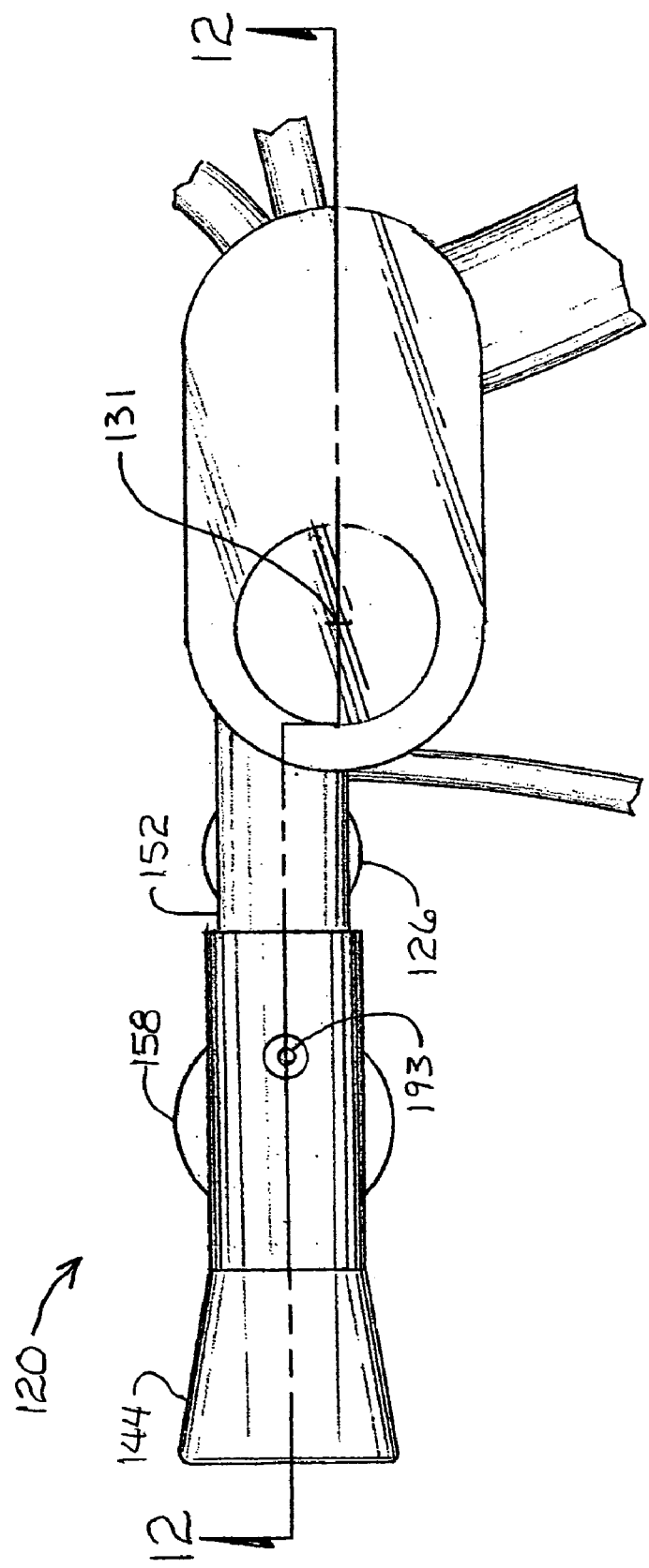
FIG. 11 is a top plan view of the enhanced condensation analyte collection of FIG. 10.
Figure 12:
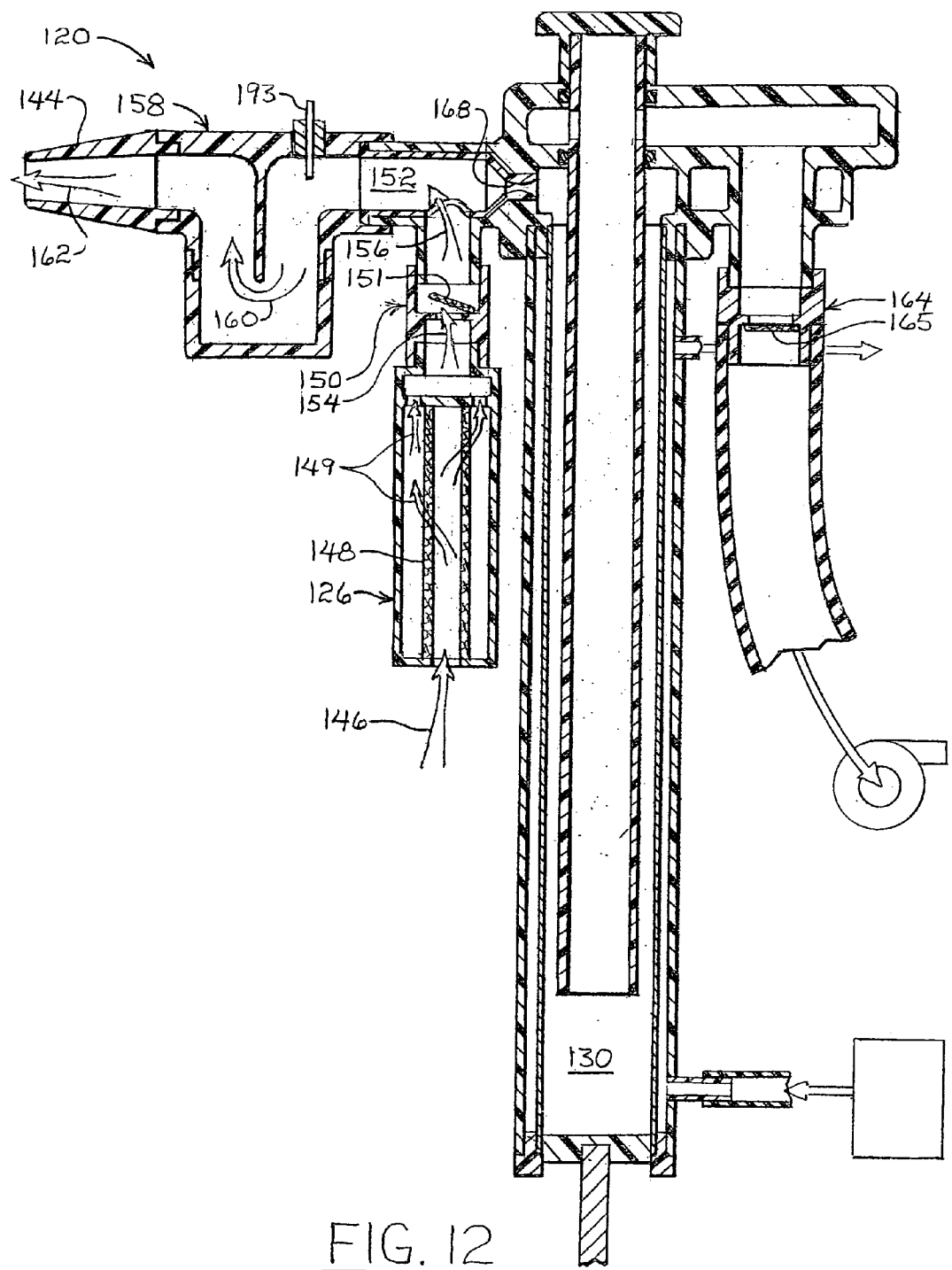
FIG. 12 is a cross-section view of the enhanced condensation analyte collector of FIGS. 10 and 11 taken along the section plane 12-12 of FIG. 11 and showing the valve positions set for inhalation mode.

Another example breath aerosol analyte collector 120, illustrated in FIGS. 10-12, enhances a different property of the exhaled breath aerosol, its mass, and then applying centrifugal force to the aerosol to facilitate collection of the exhaled breath aerosol analytes. More specifically, in this embodiment breath aerosol analyte collector 120, the conditions are created to enhance condensation of the water vapor in the exhaled breath on the aerosol particles and/or droplets to increase the mass of the aerosol, as will be explained in more detail below, and then applying centrifugal force to the aerosol with enhanced mass to enhance collection of the aerosol 121 on a condensation surface 122, as will also be described in more detail below. Then some extraction means, for example, the wiper 124, is used to extract the collected aerosol 121 from the collection surface 122, as will also be explained in more detail below.

Essentially, ambient air is preferably inhaled by the test subject (not shown) through a pre-collection filter assembly 126 to remove any ambient aerosols for the reasons explained above. Then, the breath or air is exhaled by the test subject through flow constriction, such as a jet nozzle or orifice (explained below), to create a jet stream flow into an expansion chamber and/or collection chamber (explained below) to expand, cool, and cause condensation of water vapor in the exhaled breath, and to create a spiral flow of the exhaled breath, indicated by flow arrows 128, through the collection chamber 130 to force aerosol against the tubular collection surface 122. The aerosol in the expansion chamber nucleates the water vapor condensation to add mass, as will be explained in more detail below. The spiral flow 128 creates centrifugal forces on the aerosol and condensed water, and it creates turbulences that help to break down boundary layers of fluid flow on the collection surface 122. Both of these effects enhance probability that the aerosols and condensed water in the exhaled breath will contact and be retained by the collection surface 122, as illustrated in exaggerated scale at 121. The exhaled air flow, stripped of most, if not all, of the exhaled aerosols then turns as indicated by flow arrow 129 and exhausts out of the collection chamber 130 through an exhaust tube 132, which extends longitudinally through the collection chamber 130, where the tube 132 also helps to shape and maintain the spiral flow 128. An optional cooling fluid 134 can be flowed through a space 136 between the collection tube 138 and outer shell 140 to help maintain the collection surface 122 in a desired temperature range for efficient condensation and collection of water and aerosols 121 on the collection surface 122. It is preferred, but not essential, that the exhalation of the breath be assisted by a vacuum pump 142 in order to help maintain enough of a pressure drop to enhance nucleation and condensation through the jet nozzle or orifice (explained below) without extraordinary exhaling effort by the test subject. The exhaust tube 132 is removable from the collection chamber 130 to accommodate extraction of the collected aerosols 122 by pushing the wiper 124 longitudinally through the collection chamber 130.

With reference now primarily to FIG. 12 along with secondary reference to FIG. 10, a mouthpiece 144 is provided for the test subject to inhale and exhale breaths through the aerosol analyte collector 120. Again, the mouthpiece 144 can have any shape or structure and can be part of a face mask (not shown), an endotrachial tube or any other device for capturing a test subject's breath and channeling it through components in the collector 120. Inhalation of a breath draws ambient air through the pre-collection filter assembly 126, as indicated by flow arrow 146 to remove ambient aerosols from the air being inhaled so that any aerosol analytes 121 collected on the collection surface 122 will be derived from the test subject's lungs and airway and will not be contaminated by ambient aerosols. The pre-collection filter assembly 126 is depicted for example in FIG. 12 as having a paper or cloth filter element 148 to catch ambient aerosols, but any other kind of filter technology or apparatus that is effective to catch and remove ambient aerosols from the air being inhaled can also be used for this purpose. A suitable pre-collection filter 126 for this purpose may be, for example, an Air Life™ Bacterial Viral Filter, manufacturer's part no. 001851, available from Cardinal Health, Inc. of Dublin, Ohio.

The air flows as indicated by arrows 149 through the filter assembly 126, through a first one-way check valve assembly 50 or any other suitable valve type, and into the main air duct 152, as indicated by flow arrows 154, 156. An example one-way check valve that will work for this purpose is part no. 1664 "one-way valve" available from The Hudson RCI Company, of Temecula, Calif. From the main air duct 152, the air flows backward through a classifier or trap 158, which will be explained in more detail below, and through the mouthpiece 144, as indicated by arrows 160, 162, to be inhaled by the test subject (not shown). The mouthpiece, trap, main air duct, and connecting sections are sometimes jointly or severally referred to herein as a conduit. The first valve assembly 150 opens during inhalation, as depicted diagrammatically by the open valve member 151 to allow inflow of air through the filter assembly 126, while a second one-way check valve assembly 164 closes, as indicated by the closed valve closure member 165, to prevent backflow of air through the collection chamber 130 during inhalation. Because of the small size of the jet nozzle or orifice 168, which will be explained in more detail below, the second one-way check valve may not be needed. However, if a valve 164 is needed to prevent backflow, it can be any suitable valve type to perform that function, not just a one-way check valve.

Figure 13:
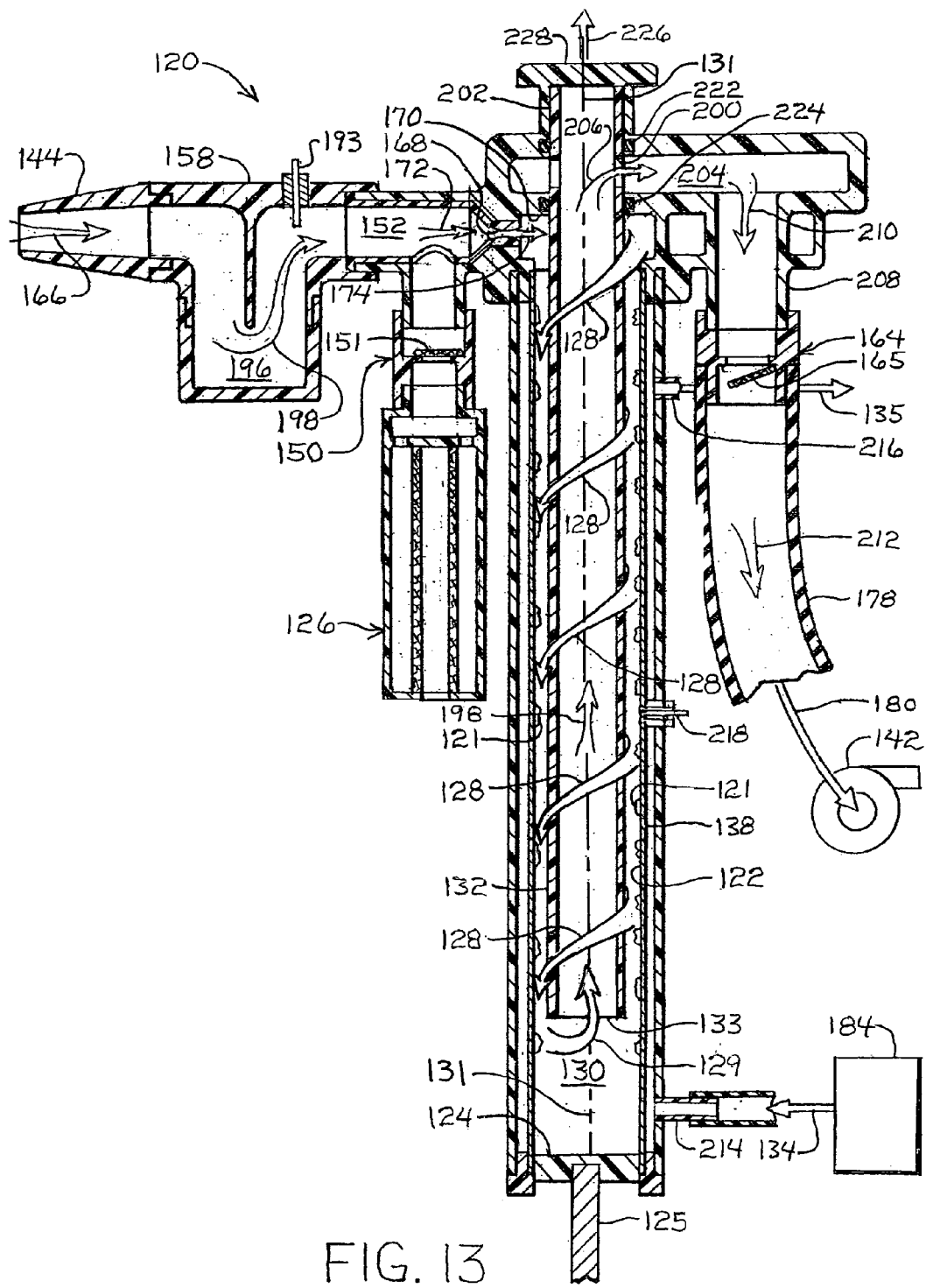
FIG. 13 is a cross-section view similar to FIG. 12, but with the valve positions reversed for exhalation mode.

Next, after inhalation as described above, the test subject exhales breath, which flows through the collector 120, as best seen in FIG. 13 with continuing secondary reference to FIG. 10. As shown in FIG. 13, the exhaled breath enters the collector 120 through the mouthpiece 144, as indicated by flow arrow 166. Upon this reversal of airflow from inhalation to exhalation, the first valve assembly 150 closes, as indicated diagrammatically by the closed valve member 151, and the second valve assembly 164 opens, as indicated diagrammatically by the opened valve member 165. This reversal of valve assemblies 150, 164 prevents the exhaled air from flowing backward through the pre-collection filter assembly 126 and directs the flow instead from the main air duct 150 through the nozzle, orifice or other flow constrictor 168 and into the expansion chamber 170 and/or collection chamber 130, as indicated by flow arrows 172, 174. As mentioned above, an optional vacuum source can be connected to an exhaust outlet conduit 178, as indicated diagrammatically by vacuum pump 142 and arrow 180, to increase and/or maintain an adequate pressure drop across nozzle 168, i.e., pressure differential between the main air duct plenum 152 and the expansion chamber 170 to get the desired cooling and nucleated condensation effect in the expansion chamber 170 without requiring extraordinary exhaling effort by the test subject. An optional pressure transducer 182 or pressure conduit 183 to such a pressure transducer (illustrated diagrammatically by pressure transducer 182 in FIG. 10) can be tapped into the main air duct plenum 152 to sense the build-up of pressure in the plenum 152 upon the start of exhalation by the test subject for any of a number of control functions. Another pressure sensor (not shown) can be tapped into the expansion chamber 170 and/or collection chamber 130 to monitor pressure in these chambers 130, 170 or pressure drop across the jet nozzle 168 for feedback control to the vacuum source 142 to increase or decrease the pressure in the expansion chamber 170 and/or collection chamber 130 as needed for the desired amount of jet cooling effect. Temperature sensors (not shown) can also be added in the plenum 152 and expansion chamber 170 for achieving the desired gas temperature differentials for a good balance between enough nucleated condensation for good exhaled breath aerosol collection without too much condensate that dilutes the collected analyte specimens. For example, the pressure increase in plenum 152 from the start of exhalation can be used to activate the vacuum source 142, to activate the cooling fluid source 184, to actuate valve 150, 164 (if they are of a type that require motive force for activation), and myriad other functions that may occur to persons skilled in the art, once they understand the principles of this invention. A microprocessor 186 can be used to facilitate these and other functions, as illustrated schematically by phantom lines 188, 189, 190, 191, 192 in FIG. 10, or by analog or other methods. Such implementations are well within the capabilities of persons skilled in the art and need not be described here for an understanding of this invention. Likewise, a number of other sensor and/or transducer technologies, such as flow meters, manual switches, and others can be used to implement these functions, as will also be understood by persons skilled in the art, once they understand the principles of this invention. For example, a carbon dioxide sensor 193 can be used to detect increase in carbon dioxide, which may indicate exhaled breath to start one or more of the functions of the collector 120. The link 194 to the microprocessor 186 in FIG. 10 is a schematic indication of control functions based on carbon dioxide detection in the air flow. One particular advantage of a carbon dioxide detector 193 is that it can distinguish between exhaled air that has been no deeper than the test subject's airway, which has near normal air content of carbon dioxide, from air that is exhaled from deep in the lungs, which has higher carbon dioxide content. Thus, for example, if the valves 150, 164 are actively controllable or actuateable, as opposed to self-actuating one-way check valves, they can be switched on or off to allow exhaled air to flow into the collection chamber 130 only when an increase in carbon dioxide indicates that breath exhaled from deep in the lungs has reached the collector 120. If it is determined that part or all of an exhaled breath is not to be accepted in the collection chamber 130 for this reason or for any other control reason (e.g., insufficient velocity or flow rate, volume control, etc.), the exhaled flow can be directed back through the pre-collection filter assembly 126 to the atmosphere, or another outlet port and valve (not shown) can be provided anywhere upstream of the jet nozzle 168 for redirecting the exhaled air out of the collector 120. For example another outlet port and valve (not shown) could be connected into or out of the main plenum 152 or the valve 150 could be a 3-way valve connected to another outlet port to divert such unwanted flow out of the system, if it is preferred to avoid such backward flow through the filter assembly 126. Of course, the microprocessor 136 or other control systems used can reverse those functions discussed above when the pressures, flows, carbon dioxide, temperatures, and the like reverse or get out of desired ranges for the functions.

Referring again primarily to FIG. 13 with secondary reference to FIG. 10, the exhaled breath 166 is preferably directed first through a classifier or trap 158 to stop and retain any large materials or artifacts (e.g., greater than about 10 microns mean equivalent diameter) in the exhaled air, such as bits of food, sputum, expectorate, saliva, and the like, which could skew collection and/or measurements of collected aerosol analytes of interest. The trap 158 in FIG. 13 is illustrated, for example, as a simple U-shaped air conduit 196, in which such large materials would be trapped, because they would have too much mass to make the U-turn illustrated by flow arrow 198 and defy gravity to get into the main air duct plenum 150. However, many other types of traps or classifiers would also work for this purpose.

As mentioned above, from the main air duct plenum 152, the air flow 172, 174 is directed through a jet nozzle or orifice 168 into the expansion chamber 170 and/or collection chamber 130. The jet nozzle or orifice 168 (not drawn to scale) is very much smaller in diameter than the plenum 152, so air flow through the jet orifice accelerates to a high velocity and then escapes in a jet stream into the lower pressure expansion chamber 170. The result of this effect is an adiabatic expansion and cooling of the fluid as it expands into the lower pressure expansion chamber 170, which causes super-saturation of water vapor in the stream of exhaled breath.

Water vapor in a rapidly cooling, super-saturated volume of carrier gas condenses upon solid and/or liquid aerosols suspended in the air flow, i.e., on the exhaled breath aerosols, which nucleate the condensation. Of course, condensation also occurs on the interior walls of the expansion chamber 170 and on the interior surface 122 of the collection chamber 130. However, a significant feature of this implementation of the invention is the creation of conditions that enhance such nucleated condensation on the exhaled breath aerosols, which adds mass to the aerosols and, thereby, renders them more susceptible to a collection force.

One of the collection forces used in this implementation of the invention is centrifugal force applied to the aerosols, which has a greater effect on the aerosols that, along with condensed water on them, have increased mass. The centrifugal force is applied in this embodiment 120 by directing the jet stream flow 174 tangentially, or offset from the longitudinal axis 131 of the collection chamber 130, into the expansion chamber 170, which, along with the low pressure created by the vacuum source 142, causes a vortical stream of the exhaled breath spiraling down the annulus between the exhaust tube 132 and the collection tube 138, as indicated by flow arrow 128. The collection chamber 130 is preferably in the shape of a figure of revolution, such as a cylinder, with a longitudinal axis 131, and the jet stream flow 174 is directed in offset relation, to the longitudinal axis 131 into the expansion chamber 170, which is merely a top part and/or top extension of the collection chamber 130. The components of the main air duct or conduit 152 intersecting the expansion chamber 170 and/or the collection chamber in a tangential manner with or without the constriction or nozzle 168 are sometimes referred to as a vortex generator. The vacuum source 142 is not essential, because the exhaled breath in the plenum 152 itself raises the pressure in the plenum above the pressure in the expansion chamber 170 and collection chamber 130, but the vacuum source 142 enhances this process and reduces the feeling of resistance to exhalation felt by the test subject. The resulting vortex 128 creates a powerful centrifugal force on the aerosol suspended in the vortical stream 128, especially those aerosols that are laden with the additional mass of the nucleated condensation, as explained above. The dwell time of the exhaled breath stream 128 in the collection chamber 130, i.e., the amount of time that it takes for an average air molecule to spiral down the vortex 128 from the expansion chamber 170 to the entrance 133 of the exhaust tube 132, depends on dimensions of the collection chamber 130 and operating pressures in the collector 120, but the centrifugal force acts on any aerosols in the vortical stream 128 all the way down the annular space to the exhaust tube entrance 133. These centrifugal forces accelerate the particles toward the condensation surface 122 of the collection tube 138. The more mass an aerosol has, the more it is accelerated toward the collection surface 122.

As mentioned above, there is also some condensation of water vapor from the exhaled breath on the collection surface 122, depending on the temperature difference between the water vapor in the exhaled breath and the collection surface 122. However, this implementation of the invention requires only enough difference in temperature between the water vapor entering the expansion chamber 170 and the temperature in the expansion chamber 170 and continuing into the collection chamber 130 (the expansion chamber 170 is merely an upper portion and/or extension of the collection chamber 130) to enable mass accretion on aerosol particles and droplets by nucleated condensation to assure capture of a consistent and majority of aerosol particles and droplets on the collection surface 122. Further increase in that temperature differential will only increase condensation of water vapor directly on the collection surface 122 and, thereby, increase dilution of the captured exhaled breath aerosol analytes on the collection surface 122 by the additional condensed water on the collection surface 122 without proportionally increasing the collected quantity of aerosol analytes. Therefore, to enable consistency and repeatability of aerosol analyte collection that can be analyzed and/or compared in a meaningful manner to other aerosol analyte collections from the same test subject and/or from other test subjects or to standards and the like, it may be important to maintain the temperature of the collection surface 122 and collection chamber 130 within a desired or prescribed temperature range. Therefore, a temperature control system may be desirable and, in the example collector 120, is illustrated as a temperature controlled cooling fluid jacket or chamber 136 between the collection tube 138 and an outer shell 140 to maintain a temperature controlled collection surface 122. The cooling fluid can be circulated from a source 184 through an inlet tube 214 into the jacket 136 and out from the jacket 136 through an outlet tube 216 at another location, as indicated by arrows 134, 135, respectively. The cooling fluid can be water supplied by a thermostatic circulator manufactured by Recirculating Chiller, Neslab Instruments, Waltham, Mass., or similar device. Any suitable thermostat 218, such as a thermocouple or other technology can be used to measure temperature of the exhaled breath flowing in the collection chamber 130 and to feed such measurements back to the microprocessor 192 or other suitable controller, as indicated schematically by link 220 (FIG. 10), to control the source 184 to produce more or less cooling as necessary to maintain the desired or prescribed temperature.

Upon entering the exhaust tube 132, as indicated by flow arrow 129, the exhaled breath flow, stripped of most, if not all, of the aerosol analytes 121, which cling to the collection surface 122, continues its flow through the exhaust tube 132, as indicated by flow arrow 198. One or more ports 200 near the top 202 of the exhaust tube 132 allow the exhaled breath to flow into an exhaust manifold chamber 204, as indicated by flow arrow 206. From the exhaust manifold chamber 204, the exhaled breath flows through an exhaust port fitting 208, as indicated by flow arrow 210, through the valve 164 and exhaust outlet conduit 178, as indicated by flow arrow 212, to the vacuum source 142. All of these exhaust components from the exhaust tube 132 to the exhaust port fitting 208 are sometimes referred to as an exhaust outlet.

Upon completion of a collection period, the exhaust tube 132, which is slidably sealed by a pair of O-rings 222, 224 or other appropriate seals, can be pulled longitudinally out of the collection chamber 130, as indicated by arrow 226 above the pull knob 228 at the top end 202 of the exhaust tube 132. Then, with the exhaust tube 132 pulled out of the collection chamber 130, the wiper 124 can be pushed by a rod 125 or other suitable device, either manually or with some machine actuator, spring, pneumatic or hydraulic actuator, etc., upwardly through the collection chamber 130 to wipe the analytes 121 off the collection surface 122. In addition to the analytes 121, there will be a significant amount of condensed water on the collection surface 122, which gets wiped along with the analytes off the surface 122 by the wiper 124 and will usually be adequate to dissolve the analytes 121 and retain them in solution. As the wiper 124 approaches the top end of the collection chamber 130, any suitable appliance or apparatus can be used to extract the condensed water and analytes from the collector 120 for further study, analysis, or other use. For example, a syringe or pipette (not shown) can be used to draw the solution containing the analytes out of the collection chamber 130 through the opening left by the removal exhaust tube 132, as will be understood by persons familiar with those kinds of instruments, or more sophisticated or automated equipment can be devised for this purpose.

The criteria for selecting particular physical dimensions and operating parameters for the collector 120 should preferably balance the efficiency and effectiveness of the aerosol collection against the dilution caused by the condensed water. It may be preferable, but not essential, that the temperature differential discussed above be increased only to the extent that further increase no longer increases the amount of detectable analytes in the collected specimen. Further, the collection chamber 130, while shown to be cylindrical, can also be conical, spherical, or any other shape, but is preferably a figure of revolution. Also, all of the control features described above, including, but not limited to, those described for the collector 10 of FIGS. 1-9 can be used in this collector embodiment 120, as will be understood by persons skilled in the art, once they understand the principles of this invention.

The foregoing description is considered as illustrative of the principles of the invention. Furthermore, since numerous modifications and changes will readily occur to those skilled in the art, it is not desired to limit the invention to the exact construction and process shown and described above. Accordingly, resort may be made to all suitable modifications and equivalents that fall within the scope of the invention. The words "comprise," "comprises," "comprising," "include," "including," and "includes" when used in this specification are intended to specify the presence of stated features, integers, components, or steps, but they do not preclude the presence or addition of one or more other features, integers, components, steps, or groups thereof.

The invention claimed is:

1. Aerosol collector apparatus for collecting aerosol from exhaled breath of a test subject, comprising:
    an aerosol collection chamber with a collection surface charged with an electrostatic voltage for collecting aerosol particles from exhaled breath, wherein the aerosol particles are ionized after being exhaled;
    a conduit for channeling the exhaled breath from the test subject to the aerosol collection chamber;
    an ionizer system in the conduit for ionizing the aerosol particles in the exhaled breath,
    an extractor system to remove the aerosol particles from the collection surface for analysis; and
    a pre-collection filter, wherein the pre-collection filter is an ionizing filter connected in fluid-flow relation to the conduit, and the pre-collection filter is positioned in close enough proximity to the aerosol collection chamber to filter ambient aerosols and prevent ambient aerosols from being inhaled by the test subject.

2. The aerosol collector apparatus of claim 1, including at least one flow meter positioned to measure flow rate of the exhaled breath through the chamber.

3. The aerosol collector apparatus of claim 1, including a wiper in the extractor system, which is positioned slideably on the collection surface for wiping the collected aerosol particles off the collector surface.

4. The aerosol collector apparatus of claim 1, including an exhaust outlet in fluid-flow relation to the collection chamber to remove exhaled breath stripped of aerosol particles.

5. The aerosol collector apparatus of claim 4, including a vacuum source connected to the exhaust outlet.

6. The aerosol collector apparatus of claim 1, including a mouthpiece connected in fluid-flow relation to the conduit.

7. The aerosol collector apparatus of claim 6, including an artifact trap positioned in the conduit between the mouthpiece and the collection chamber.

8. The aerosol collector apparatus of claim 6, including a mouthpiece in the conduit upstream from the collection surface.

9. The aerosol collector apparatus of claim 1, including operable valves so that during inhalation of a breath by the test subject through the mouthpiece the inhalation breath flows through the pre-collection filter, and so that during exhalation of breath by the test subject the exhalation breath flows through the collection chamber.

10. The aerosol collector apparatus of claim 9, including a flow meter connected in fluid-flow relation to the collection chamber to produce flow rate measurements of exhaled breath, and wherein a control means utilizes the flow rate measurements of the exhaled breath to partially open or partially close operable valves to control flow rate of exhaled breath.

11. The aerosol collector apparatus of claim 1 wherein the ionizer system is positioned in a conduit upstream from the collection surface.

12. The aerosol collector apparatus of claim 11, wherein the ionizer system is positioned in the conduit downstream of the mouthpiece.

13. The aerosol collector apparatus of claim 12, including a wire mesh positioned in the conduit between the ionizer assembly and the mouthpiece.

14. Aerosol collector apparatus for collecting aerosol from exhaled breath of a test subject, comprising:
    an aerosol collection chamber in fluid-flow relation to a vortex generator for collecting aerosol particles from exhaled breath, wherein the aerosol particles are subject to nucleation condensation after being exhaled;
    a conduit for channeling the exhaled breath from the test subject to the aerosol collection chamber;
    an extractor system to remove the aerosol particles from the collection surface for analysis; and
    a pre-collection filter, wherein the pre-collection filter is an ionizing filter connected in fluid-flow relation to the collection chamber, and wherein the pre-collection filter is positioned in close enough proximity to the aerosol collection chamber to filter ambient aerosols and prevent them from being inhaled by the test subject.

15. The aerosol collector apparatus of claim 14, wherein the collection chamber is a figure of revolution with a longitudinal axis, and wherein the vortex generator includes a tangential intersection of the conduit with the collection chamber.

16. The aerosol collector apparatus of claim 15, wherein the vortex generator also includes a flow constriction at the intersection of the conduit with the collection chamber in a position to direct the exhaled breath through the flow constriction to produce a jet stream that is laterally offset from the longitudinal axis of the collection chamber.

17. The aerosol collector apparatus of claim 16, wherein the flow construction includes a nozzle.

18. The aerosol collector apparatus of claim 14, wherein the collection surface is temperature controlled to maintain the temperature of the collection surface within a predetermined temperature range.

19. The aerosol collector apparatus of claim 14, including at least one flow meter positioned to measure flow rate of the exhaled breath through the chamber.

20. The aerosol collector apparatus of claim 14, including a wiper in the extractor system, which is positioned slideably on the collection surface for wiping the collected aerosol particles off the collector surface.

21. The aerosol collector apparatus of claim 14, including an exhaust outlet in fluid-flow relation to the collection chamber to remove exhaled breath stripped of aerosol particles.

22. The aerosol collector apparatus of claim 21, including a vacuum source connected to the exhaust outlet.

23. The aerosol collector apparatus of claim 14, including a mouthpiece connected in fluid-flow relation to the collection chamber.

24. The aerosol collector apparatus of claim 23, including an artifact trap positioned in the conduit between the mouthpiece and the collection chamber.

25. The aerosol collector apparatus of claim 23, including a mouthpiece in the conduit upstream from the collection surface.

26. The aerosol collector apparatus of claim 25, including a wire mesh positioned in the conduit between the ionizer assembly and the mouthpiece.

27. The aerosol collector apparatus of claim 14, including operable valves so that during inhalation of a breath by the test subject through the mouthpiece the inhalation breath flows through the pre-collection filter, and so that during exhalation of breath by the test subject the exhalation breath flows through the collection chamber.

28. The aerosol collector apparatus of claim 14, including a flow meter connected in fluid-flow relation to the collection chamber to produce flow rate measurements of exhaled breath, and wherein a control means utilizes the flow rate measurements of the exhaled breath to partially open or partially close operable valves to control flow rate of exhaled breath.

29. Aerosol collector apparatus for collecting aerosol from exhaled breath of a test subject, comprising:

an aerosol collection chamber with a collection surface for collecting aerosol particles from exhaled breath, wherein the exhaled aerosol particles are subjected to an electrostatic, centrifugal, thermophoretic, magnetic, gravitational, inertia or aerodynamic force to capture substantially all aerosol materials as small as 10 nanometers in mean equivalent diameter for analysis;

a conduit for channeling the exhaled breath from the test subject to the aerosol collection chamber;

an extractor system to remove the aerosol particles from the collection surface for analysis;

a pre-collection filter positioned in close enough proximity to the aerosol collection chamber to filter ambient aerosols and prevent ambient aerosols from being inhaled by the test subject, and at least one flow meter positioned to measure flow rate of the exhaled breath through the collection chamber wherein a control means utilizes the flow rate measurements of the exhaled breath to partially open or partially close operable valves to control flow rate of exhaled breath.

30. The aerosol collector apparatus of claim 29 wherein the collection chamber includes an ionizer system.

31. The aerosol collector apparatus of claim 29 wherein the collection chamber includes a vortex generator.

32. The aerosol collector apparatus of claim 29 wherein the pre-collection filter is an ionizing filter.

* * * * *